United States Patent [19]

Paioni et al.

[11] 4,259,338
[45] Mar. 31, 1981

[54] BENZOFURANYL-TETRAHYDROPYRIDINES AND -PIPERIDINES, THEIR ACID ADDITION SALTS AND ANTIDEPRESSANT PREPARATIONS THEREOF

[75] Inventors: Romeo Paioni, Reinach; Walter Schilling, Himmelried; Raymond Bernasconi, Oberwill, all of Switzerland

[73] Assignee: Ciba-Geigy Corporation, Ardsley, N.Y.

[21] Appl. No.: 140,405

[22] Filed: Apr. 14, 1980

Related U.S. Application Data

[63] Continuation-in-part of Ser. No. 49,006, Jun. 15, 1979, abandoned.

[30] Foreign Application Priority Data

Jun. 22, 1978 [CH] Switzerland ............... 6823/78

[51] Int. Cl.³ ............... A61K 31/445; A61K 31/44; C07D 405/02
[52] U.S. Cl. ............... 424/267; 260/346.22; 260/346.71; 260/346.73; 424/263; 546/196; 546/269
[58] Field of Search ............... 546/196, 269; 424/263, 424/267

[56] References Cited

U.S. PATENT DOCUMENTS

| | | | |
|---|---|---|---|
| 2,633,468 | 3/1953 | Pohland | 546/196 |
| 3,470,192 | 9/1969 | Binon et al. | 546/269 |
| 3,751,390 | 8/1973 | Hopps et al. | 546/196 X |
| 3,853,899 | 12/1974 | Fake | 546/269 |
| 3,890,441 | 6/1975 | Schenker et al. | 424/267 |
| 4,154,743 | 5/1979 | Bosshard et al. | 546/196 X |

FOREIGN PATENT DOCUMENTS

| | | |
|---|---|---|
| 1620315 | 4/1970 | Fed. Rep. of Germany . |
| 2653147 | 6/1977 | Fed. Rep. of Germany . |
| 1139146 | 1/1969 | United Kingdom ............... 546/196 |
| 1465167 | 2/1977 | United Kingdom . |
| 1465581 | 2/1977 | United Kingdom . |
| 1510977 | 5/1978 | United Kingdom . |

OTHER PUBLICATIONS

Ziegler, H., et al., *Chim. Ther.*, 6, 159–166 (1971).
Takamatsu, K., et al., *J.C.S. Chem. Comm.*, 903–904 (1973).
Takamatsu, K., et al., *J. Org. Chem.*, 41, 541–543 (1976).
*Chemical Abstracts*, 67:82013b (1967) [Yoshiyuki et al., *Bull. Chem. Soc. Jap.*, 40, 1224 (1967)].
Gilman, H. et al., *J. Am. Chem. Soc.*, 57, 2095–2099 (1935).
*Chemical Abstracts*, 63:16319c (1965) [Royer et al., *Bull. Chem. Soc. Fr.* 1965, 9, 2607].
Queval, P., et al., *Eur. J. Med. Chem.—Chim. Ther.*, 1974 (3), 9, 335–340.
*Chemical Abstracts*, 65:16925g (1966) [Goldenberg et al., *Chim. Ther.* 1966 (4), 221–227].
Krapcho, A., et al., *Tett. Lett.* No. 12, 957–960 (1973).
*Chemical Abstracts*, 64:19580b (1966) [Pene et al., *Bull. Soc. Chim. Fr.*, 1966 (2), 586–594].
*Chemical Abstracts*, 13:2025 (1919) [Adams et al., *J. Am. Chem. Soc.*, 41, 648–670 (1919)].
Claisen, L., *Chem. Ber.*, 53, 322–325 (1920).
Noyce, D. et al., *J. Org. Chem.*, 37, 4313 (1972).
Worden, L., et al., *J. Org. Chem.*, 34, 2311–2313 (1969).
McElvain, S., et al., *J. Am. Chem. Soc.*, 70, 1826 (1948).
Paul, R., et al., *Bull. Soc. Chim. Fr.*, 1954, 982, 985.
Heimgartner, H. et al., *Helv. Chim. Acta*, 55, 1133 (1972).
McCarthy, J., et al., *Tett. Lett.* No. 52, 5183–5186 (1978).
*Chemical Abstracts*, 71:61198h (1969) [France 1,537.206, 8/23/68].

*Primary Examiner*—Henry R. Jiles
*Assistant Examiner*—Richard A. Schwartz
*Attorney, Agent, or Firm*—Theodore O. Groeger

[57] ABSTRACT

The present invention provides new benzofuranyl-tetrahydropyridines and -piperidines of the general formula I

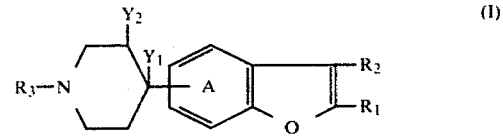

in which $R_1$ and $R_2$ independently of one another are hydrogen or lower alkyl or together are lower alkylene, $R_3$ is hydrogen, lower alkyl, lower alkenyl, lower alkynyl, cyclo-lower alkyl or cyclo-lower alkyl-lower alkyl and $Y_1$ and $Y_2$ are each hydrogen or together are an additional bond, and the ring A is not further substituted or is further substituted by lower alkyl, lower alkoxy, halogen with an atomic number not more than 35, cyano or hydroxyl and the pharmaceutically acceptable acid addition salts thereof, and antidepressant preparations containing these compounds. The compounds according to the invention have valuable pharmacological properties. In particular, they inhibit the absorption of serotonin by mesencephalic synaptosomes, the serotonin depletion induced in the brain of rats by H 75/12, the absorption of noradrenalin by mesencephalic synaptosomes in rats and the noradrenalin depletion induced in the brain of rats by H 77/77. In the same dosage they also effect inhibition of monoamino-oxidase in the brain of rats and in the liver of rats. Furthermore, they intensify the "head twitch" induced by 5-hydroxy-tryptophan, and are distinguished by good tolerance. The compounds of the general formula I and their pharmaceutically acceptable acid addition salts can therefore be used as psychopharmaceuticals and in particular as antidepressants.

26 Claims, No Drawings

BENZOFURANYL-TETRAHYDROPYRIDINES AND -PIPERIDINES, THEIR ACID ADDITION SALTS AND ANTIDEPRESSANT PREPARATIONS THEREOF

This is a continuation in part of our application Ser. No. 49,006 filed June 15, 1979, now abandoned.

The present invention relates to new benzofuranyl-tetrahydropyridines and -piperidines of the general formula I

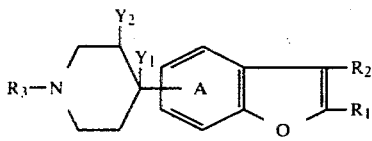

in which $R_1$ and $R_2$ independently of one another are hydrogen or lower alkali or together are lower alkylene, $R_3$ is hydrogen, lower alkyl, lower alkenyl, lower alkynyl, cyclo-lower alkyl or cyclo-lower alkyl-lower alkyl and $Y_1$ and $Y_2$ are each hydrogen or together are an additional bond, and the ring A is not further substituted or is further substituted by lower alkyl, lower alkoxy, halogen with an atomic number not more than 35, cyano or hydroxyl.

The invention likewise relates to the acid addition salts, especially the pharmaceutically acceptable acid addition salts, of compounds of the general formula I.

In this specification "lower" organic compounds and radicals derived from these are understood as meaning in particular those compounds and radicals which contain not more than 7 and in particular not more than 4 carbon atoms.

The ring A can contain, as further substituents, for example lower alkyl, lower alkoxy, halogen with an atomic number of not more than 35, cyano, hydroxyl or trifluoromethyl and preferably contains not more than one of the three last-mentioned radicals and not more than three, preferably not more than two and in particular not more than one of the other radicals. The total number of further substituents in the ring A can be three, but preferably not more than two further substituents are present. In particular, the invention relates to compounds of the general formula I in which the ring A contains one further substituent or no further substituents.

As $R_1$ or $R_2$ and as a substituent of the ring A, lower alkyl contains, for example, not more than 7 and in particular not more than 4 carbon atoms and can be branched and bonded in any position, but is preferably straight-chain. Examples are, in particular, butyl, isobutyl, tert.-butyl, propyl, isopropyl and especially ethyl and methyl.

Lower alkylene formed by $R_1$ and $R_2$ together can contain 3 to 7 and preferably 3 to 5 carbon atoms and is, for example, trimethylene, pentamethylene and in particular tetramethylene.

As a substituent of the ring A, lower alkoxy contains, for example, not more than 7 and in particular not more than 4 carbon atoms and can be branched, in which case the oxygen can be bonded in any position, but is preferably straight-chain. Examples are butoxy, propoxy, isopropoxy, ethoxy and especially methoxy.

As a substituent of the ring A, halogen is, for example, halogen with an atomic number of not more than 35, i.e. fluorine, chlorine or bromine.

Lower alkenyl $R_3$ contains not more than 7 and in particular 3 to 5 carbon atoms and, as in the case of lower alkynyl $R_3$ also, the multiple bond is preferably not located at the carbon atom bonded to the nitrogen atom. For example, lower alkenyl $R_3$ is 1-methyl-allyl, 3-methyl-2-butenyl, especially 2-butenyl or 2-methylallyl and in particular allyl. Lower alkynyl $R_3$ contains not more than 7 and preferably 3 to 4 carbon atoms and is, for example, 2-butynyl and especially 2-propynyl.

Cycloalkyl $R_3$ preferably contains 3 to 7 carbon atoms and is, for example, cyclopentyl, cyclohexyl, cycloheptyl and in particular cyclopropyl.

Cycloalkyl-lower alkyl $R_3$ preferably contains 4 to 9 carbon atoms and is, for example, cyclopropylethyl, cyclobutylmethyl, cyclopentylmethyl, cyclopentylethyl, cyclohexylmethyl, cyclohexylethyl, cycloheptylmethyl or cycloheptylethyl and especially cyclopropylmethyl.

The compounds of the general formula I and their pharmaceutically acceptable acid addition salts have valuable pharmacological properties. Thus, they have a pronounced inhibitory action on the adsorption of serotonin by mesencephalic synaptosomes, and this can be demonstrated, for example, in rats on oral administration of doses of about 3 to about 100 mg/kg. In the same dosage, they also inhibit the serotonin depletion induced in the brain of rats by H 75/12. Furthermore, on oral administration in doses of about 3 to about 100 mg/kg they inhibit the adsorption of noradrenalin by mesencephalic synaptosomes in rats and the noradrenalin depletion induced in the brain of rats by H 77/77. In the same dosage they also effect inhibition of monoamino-oxidase in the brain of rats and in the liver of rats and this can be demonstrated using $^{14}$C-serotonin and $^{14}$C-phenethylamine as substrates. On intraperitoneal administration to mice in doses of about 3 to about 100 mg/kg, they also intensify the "head twitch" induced by 5-hydroxy-tryptophan. Moreover, they are distinguished by good tolerance. The novel compounds of the general formula I and their pharmaceutically accpetable acid addition salts can therefore be used as psychopharmaceuticals and in particular as antidepressants, for example for the treatment of emotional depressions.

The invention relates especially to compounds of the general formula I in which $R_1$, $R_2$, $R_3$, $Y_1$ and $Y_2$ are as defined under formula I and the ring A is not further substituted or is further monosubstituted by lower alkyl, lower alkoxy, halogen with an atomic number of not more than 35, cyano or hydroxyl, and the acid addition salts thereof. In particular, the invention relates to compounds of the general formula I in which $R_1$ is methyl and $R_2$ is hydrogen or methyl, or $R_1$ and $R_2$ together are tetramethylene, $R_3$, $Y_1$ and $Y_2$ are as defined under formula I and the ring A is not further substituted or is further monosubstituted by lower alkyl, lower alkoxy, halogen with an atomic number of not more than 35, cyano or hydroxyl, and the acid addition salts thereof. The invention relates very particularly to compounds of the general formula I in which $R_1$ is methyl and $R_2$ is methyl or hydrogen, or $R_1$ and $R_3$ together are tetramethylene, $R_3$ is as defined under formula I and is preferably hydrogen or radicals according to the definition which have not more than 4 carbon atoms, and specifically as lower alkenyl is in particular allyl, as lower alkynyl is in particular 2-propynyl, as cycloalkyl is in particular cyclopropyl and as cycloalkyl-lower alkyl is in particular cyclopropylmethyl, $Y_1$ and $Y_2$ are as defined under formula I and the ring A is not further substituted or is further monosubstituted by lower alkyl, especially methyl, lower alkoxy, especially methoxy, halogen with an atomic number of not more than 35 or cyano, and the acid addition salts thereof. The invention relates primarily to compounds of the general formula I in which $R_1$ and $R_2$ are each methyl or together are tetramethylene, $R_3$ is lower alkyl, especially methyl, or lower alkynyl, especially 2-propynyl, or in particular hydrogen and $Y_1$ and $Y_2$ togther are an additional bond or preferably are each a hydrogen atom, the ring A is not further substituted or is further monosubstituted by methyl, methoxy, halogen with an atomic number of not more than 35 or cyano, and the nitrogen-containing ring is preferably in the 5-position or 6-position of the benzofuran ring system and the substituent which may be present is preferably in the 7-position of the benzofuran ring system, and acid addition salts thereof, for example 4-(2,3-dimethyl-5-benzofuranyl)-piperidine, 4-(2,3-dimethyl-6-benzofuranyl)-piperidine and 4-(6,7,8,9-tetrahydro-2-dibenzofuranyl)-piperidine and the acid addition salts thereof, preferred acid addition salts in all cases being the pharmaceutically acceptable salts.

The novel tetrahydropyridine and piperidine derivatives of the general formula I and their acid addition salts can be prepared by methods known per se, for example by (a) in a compound of the general formula II

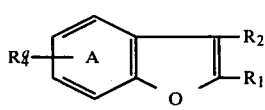
(II)

in which $R_4{}^a$ is a 1,2,3,6-tetrahydro-4-pyridyl or 4-piperidyl radical, which is unsubstituted or substituted on at least one of the ring carbon atoms adjacent to the nitrogen atom by a divalent radical $X_a$ which is replaceable by two hydrogen atoms, and to the nitrogen atom of which a radical $R_3$, according to the definition, which is unsubstituted or substituted in its 1-position by a radical $X_a$, according to the definition, or a carbon atom which carries a radical $X_a$, according to the definition, and lower alkoxy is bonded, with the proviso that, in total, at least one radical $X_a$ according to the definition must be present, $R_1$ and $R_2$ are as defined under formula I and the ring A is not further substituted or is further substituted, replacing the radical or radicals, $X_a$ and, if present, the abovementioned lower alkoxy, by hydrogen, or (b) in a compound of the general formula III

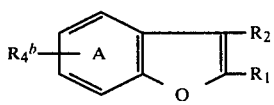
(III)

in which $R_4{}^b$ is a 4-pyridyl radical, which can be partially hydrogenated and carry the radical $R_3$ on the nitrogen atom, which can be quaternary, and $R_1$ and $R_2$ are as defined under formula I and the ring A is not further substituted or is further substituted, reducing the radical $R_4{}^b$ to a 1,2,3,6-tetrahydro-4-pyridyl or 4-piperidyl radical substituted in the 1-position by $R_3$, or (c) in a compound of the general formula IV

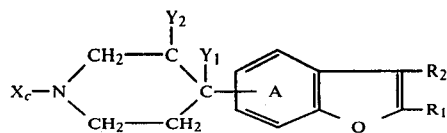
(IV)

in which $X_c$ is a radical replaceable by hydrogen and $R_1$, $R_2$, $Y_1$ and $Y_2$ are as defined under formula I and the ring A is not further substituted or is further substituted, replacing the radical $X_c$ by hydrogen, or (d) detaching the compound of the formula $$H\text{-}X_d \qquad (VI)$$

from a compound of the general formula V

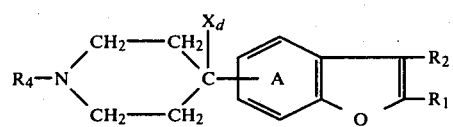
(V)

in which $X_d$ is free or esterified hydroxyl and $R_1$, $R_2$ and $R_3$ are as defined under formula I and the ring A is not further substituted or is further substituted, or (e) in a compound of the general formula VII

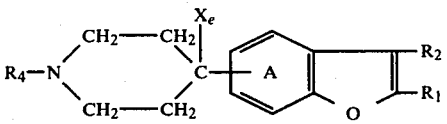
(VII)

in which $X_e$ is a radical replaceable by hydrogen and $R_1$, $R_2$ and $R_3$ are as defined under formula I and the ring A is not further substituted or is further substituted, replacing the radical $X_e$ by hydrogen, or (f) cyclising a compound of the general formula VIII

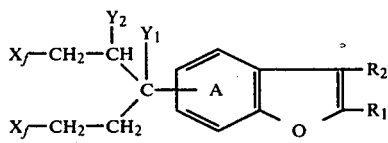
(VIII)

in which one of the symbols $X_f$ is the group $-NHR_3$, in which $R_3$ is as defined under formula I, and the other is a reactive esterified hydroxyl group, and $R_1$, $R_2$, $Y_1$ and $Y_2$ are as defined under formula I and the ring A is not further substituted or is further substituted, or (g) reacting a compound of the general formula IX

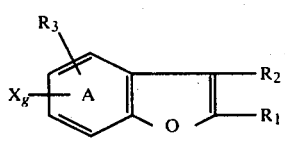
(IX)

and a compound of the general formula X

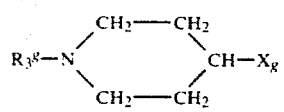

with one another, in which formulae one of the symbols $X_g$ is a halogeno-magnesium radical or an alkali metal radical and the other is halogen, $R_3{}^g$ is a radical corresponding to the definition given for $R_3$ under formula I, with the exception of hydrogen, and $R_1$ and $R_2$ are as defined under formula I and the ring A is not further substituted or is further substituted, or (h) allowing a proton acid to act on a mixture of a compound of the general formula XI

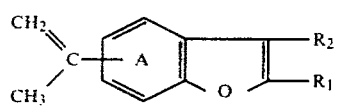

in which $R_1$ and $R_2$ are as defined under formula I and the ring A is not further substituted or is further substituted, a compound of the general formula XII

    (XII)

in which $R_3$ is as defined under formula I, and at least twice the molar amount of formaldehyde, or on the crude reaction product obtainable from the abovementioned three reactants, and/or, if desired, introducing a radical $R_3$ which differs from hydrogen into a compound of the general formula I in which $R_3$ is hydrogen and $R_1$, $R_2$, $Y_1$ and $Y_2$ are as defined under formula I, and/or, if desired, reacting a compound of the general formula I in which the ring A is substituted by bromine and the radical $R_3$ differs from hydrogen, whilst $R_1$, $R_2$, $Y_1$ and $Y_2$ are as defined under formula I, or a corresponding compound containing iodine in place of bromine, with a metal cyanide, and/or, if desired, treating a compound of the general formula I in which the ring A is substituted by lower alkoxy, whilst $R_1$, $R_2$, $R_3$, $Y_1$ and $Y_2$ are as defined under formula I, or a corresponding compound containing substituted or unsubstituted benzyloxy in place of lower alkoxy, with an ether-splitting agent, and/or, if desired, converting a compound of the general formula I in another manner known per se into another compound of the general formula I and/or separating a mixture of isomers (mixture of racemates) which is obtainable into the pure isomers (racemates) and/or resolving a racemate which is obtainable into the optical antipodes and/or converting a free compound which is obtainable into a salt or converting a resulting salt into the free compound or into another salt.

In the starting materials of the general formula II, the radicals $X_a$ which are replaceable by two hydrogen atoms are, for example, oxo or thioxo radicals. In this case, the radical $R_4{}^a$ preferably has the partial formula IIa

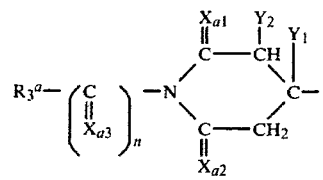

in which at least one of the symbols $X_{a1}$, $X_{a2}$ and $X_{a3}$ is an oxo or thioxo radical and the remaining symbol or symbols is or are each two hydrogen atoms, $R_3{}^a$ is hydrogen or a radical which corresponds to the definition for $R_3$ but if n is one contains one methylene group less, or, if n is one and $X_{a3}$ is oxo, lower alkoxy, and thus together with $CX_{a3}$ lower alkoxycarbonyl, and n is nought or one and $Y_1$ and $Y_2$ are as defined under formula I.

In starting materials of the general formula II in which radicals $X_a$ are oxo radicals and/or in which lower alkoxycarbonyl is located on the ring nitrogen atom, it is possible, in a manner known per se, to replace the oxo radicals by hydrogen and/or to reduce lower alkoxycarbonyl to methyl, for example by reduction with hydride reducing agents, for example with alkali metal/alkaline earth metal hydrides, such as lithium aluminium hydride, sodium bis(2-methoxyethoxy)-aluminium hydride or sodium tris-(2-methoxyethoxy)-aluminium hydride, or borane or diborane, in an ether-like solvent, such as diethyl ether, tetrahydrofuran, dibutyl ether or diethylene glycol diethyl ether, or mixtures thereof, for example at temperatures between about 0° and 100° C. or at the boiling point of the solvent used, if this is below 100° C., and preferably at about 20° C. to about 65° C.

The replacement of thioxo radicals $X_a$ by hydrogen can also be effected in a manner known per se, for example by reacting corresponding starting materials of the general formula II with Raney nickel, preferably in the presence of suitable inert organic solvents and/or diluents, such as ethanol, methanol or acetone, for example at temperatures between 0° and the boiling point of the reaction medium and preferably at room temperature up to about 80° C. or the boiling point of the reaction medium.

In the starting materials of the general formula III, the radical $R_4{}^b$ is, for example, a 4-pyridyl radical or has one of the partial formulae IIIa or IIIb

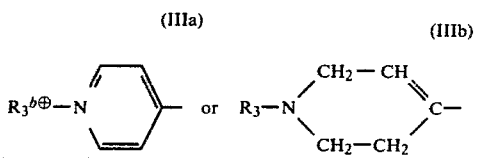

in which $R_3{}^b$ is a radical having the meaning defined for $R_3$ under formula I, with the exception of hydrogen, and $R_3$ is as defined under formula I. Compounds of the general formula III which contain a radical of the partial formula IIIb as $R_4{}^b$ already fall under the general formula I. The reduction of compounds such as those containing 4-pyridyl or a radical of the partial formula IIIa as $R_4{}^b$ to compounds of the general formula I in which $Y_1$ and $Y_2$ are hydrogen can be carried out, for example, by means of catalytically activated hydrogen using conventional hydrogenation catalysts, for example noble metal catalysts, such as palladium-on-charcoal or platinum oxide, rhodium catalysts, such as rhodium-on-charcoal or rhodium-on-aluminium oxide, or alloy skeleton catalysts, such as Raney nickel, in an inert organic solvent, such as methanol, ethanol or dioxan, at room temperature and normal pressure or at moderately elevated temperatures of up to about 100° C. and under elevated pressure of up to about 100 bars.

Starting materials of the general formula III in which $R_4{}^b$ is a radical of the partial formula IIIa can also be reduced in a manner known per se to the corresponding compounds which contain a radical of the partial formula IIIb as the radical $R_4{}^b$ and fall under the general formula I. This reduction is preferably carried out with the aid of sodium borohydride or potassium borohydride in an organic-aqueous medium, by, for example, adding an aqueous solution of sodium borohydride gradually to a solution, which has been initially introduced, of the corresponding starting material of the general formula III in an organic, water-miscible solvent, for example in a lower alkanol, such as methanol or ethanol, or mixtures thereof with water, and then allowing the reaction mixture to continue to react for some time, a reaction temperature of between about 5° and 60° C. and preferably of room temperature to 35° C. being maintained. The preparation of the starting materials of the general formula III is explained below.

In the starting materials of the general formula IV for process (c) radicals $X_c$ replaceable by hydrogen are, for example, radicals which can be replaced by hydrogen by means of solvolysis, especially hydrolysis or aminolysis or ammonolysis, or by means of reduction.

Radicals replaceable by hydrogen by means of solvolysis are, for example, acyl radicals, such as acyl radicals of organic acids, for example lower alkanoyl radicals, which can be halogenated, such as fluorinated, for example butyryl, propionyl, acetyl or trifluoroacetyl, or benzoyl radicals, or carboxyl groups, which can be functionally modified, for example esterified carboxyl groups, such as alkoxycarbonyl radicals, for example the tert.-butoxycarbonyl radical or the methoxycarbonyl radical, aralkoxycarbonyl radicals, such as phenyl-lower alkoxycarbonyl radicals, for example carbobenzoxy, and also cyano radicals or halogenocarbonyl radicals, for example the chlorocarbonyl radical, β-arylsulfonylethoxycarbonyl radicals, such as β-toluenesulfonyl- or β-bromobenzenesulfonyl-ethoxycarbonyl, or β-arylthioethyl or β-arylsulfonylethyl radicals, such as β-(p-toluenesulfonyl)ethyl or 2-(p-tolylthio)-ethyl radicals, or silyl radicals, such as the trimethylsilyl radical.

Radicals detachable by reduction are, for example, α-arylalkyl radicals, such as benzyl radicals, or α-aralkoxycarbonyl radicals, such as benzyloxycarbonyl radicals, arylsulfonyl radicals, for example p-toluenesulfonyl radicals, or 2-halogeno-alkoxycarbonyl radicals, such as the 2,2,2-trichloroethoxycarbonyl, 2-iodoethoxycarbonyl or 2,2,2-tribromoethoxycarbonyl radical.

The hydrolysis of compounds of the general formula IV can be carried out in an alkaline or acid medium. For example, it is effected by prolonged heating with an alkali metal hydroxide, especially sodium hydroxide or potassium hydroxide, in a hydroxy compound in the presence of a little water at temperatures between about 80° and 200° C. A suitable reaction medium is, for example, ethylene glycol or a lower monoalkyl ether thereof, and also, when the hydrolysis is carried out in a closed vessel, a lower alkanol, such as methanol, ethanol or butanol. Furthermore, in particular the compounds of the general formula IV in which the radical $X_c$ is a cyano group, i.e. the acyl radical of cyanic acid, or a chlorocarbonyl group can also be hydrolysed by heating with a mineral acid in an organic-aqueous or aqueous medium, for example by boiling for several hours in a mixture of 85% phosphoric acid and formic acid or by warming for several hours at about 60°–100° C. and preferably 60°–70° C. in 48% hydrobromic acid (or in hydrobromic acid) or in a hydrobromic acid/acetic acid mixture.

Further detachable groups $X_c$ are the groups formed by adding a methyl group, which is present in place of $X_c$, onto a di-lower alkyl azodicarboxylate, which groups are preferably detached by hydrolysis in an acid medium, especially by boiling in dilute, for example 1 N, hydrochloric acid, the di-lower alkyl hydrazodicarboxylate being liberated.

A radical detachable by solvolysis is, for example, the tert.-butoxycarbonyl radical, which can be detached under anhydrous conditions by treatment with a suitable acid, such as trifluoroacetic acid.

The aminolysis or ammonolysis can be carried out in a conventional manner, for example by reaction with ammonia or an amine, such as hydrazine or a mono- or dialkylamine or alkyleneamine or oxa-, aza- or thia-alkyleneamine, for example with ammonia, hydrazine, methylamine or dimethylamine, morpholine or piperidine, if necessary in an inert solvent and/or at elevated temperature.

Radicals $X_c$ which are replaceable by hydrogen by means of reduction are, for example, α-arylalkyl radicals, such as the benzyl radical, or α-aralkoxycarbonyl radicals, such as the benzyloxycarbonyl radical, which can be replaced by hydrogen in a conventional manner by means of hydrogenolysis, for example by means of hydrogen in the presence of a hydrogenation catalyst, for example platinum, palladium or Raney nickel, and, if desired, in the presence of hydrogen chloride, at room temperature and normal pressure or at moderately elevated temperatures and pressures in suitable organic solvents, for example methanol, ethanol or dioxan. Further radicals $X_c$ which are replaceable by hydrogen by means of reduction are, for example, 2-halogeno-alkoxycarbonyl radicals, such as the 2,2,2-trichloroethoxycarbonyl radical or the 2-iodoethoxy- or 2,2,2-tribromoethoxy-carbonyl radical, which can be removed in a conventional manner, especially by metallic reduction (so-called nascent hydrogen). Nascent hydrogen can be obtained by the action of metal or metal alloys, such as amalgams, on hydrogen donors, such as carboxylic acids, alcohols or water, and in particular it is suitable to use zinc or zinc alloys together with acetic acid. The reduction of 2-halogeno-alkoxy-carbonyl radicals can also be effected by means of chromium-II compounds, such as chromium-II chloride or chromium-II acetate.

A radical $X_c$ which is detachable by reduction can also be a sulfonyl group, such as a lower alkanesulfonyl group or an arylsulfonyl group, for example methanesulfonyl or p-toluenesulfonyl, and these can be detached in a conventional manner by reduction with nascent hydrogen, for example by an alkali metal, such as lithium or sodium, in liquid ammonia, or electrolytically.

If $X_d$ in the starting materials of the general formula V is free hydroxyl, process (d) is a dehydration, which, for example, can be effected by warming the corresponding starting materials, the water formed advantageously being separated off and the reaction preferably being carried out in the presence of a strong acid, for example of concentrated hydrochloric acid in glacial acetic acid or of sulfuric acid, which is used as the concentrated acid but in small amounts, or of p-toluenesulfonic acid. The dehydration can also be carried out by heating in an inert organic solvent, for example in a water-immiscible solvent, such as toluene or xylene, at the boiling point thereof, the water advantageously being separated off, or in hexamethylphosphoric acid triamide, for example at temperatures of between 180° and 240° C.

Further suitable dehydrating agents are, for example, inorganic acid anhydrides, such as phosphorus pentoxide or boron oxide, certain organic acids, such as formic acid and oxalic acid, acid salts of strong acids, such as potassium bisulfate, or ion exchange resins, for example condensation products of phenolsulfonic acids and formaldehyde.

If $X_d$ in the starting materials of the general formula V is esterified hydroxyl, for example acetoxy, benzoyloxy, methanesulfonyloxy or halogen, especially chlorine or bromine, an acid is detached as the compound of the general formula VI. This can likewise be effected by simple heating, and if desired the corresponding acid addition salt of the desired compound of the general formula I is obtained as the reaction product. If desired, the acid is detached in a hot alkaline or acid medium, for example with alkali metal hydroxides in an aqueous or lower alkanolic medium or with nitrogen bases, such as piperidine, pyridine, lutidine, collidine or quinoline, or with polyphosphoric acid. The esterified hydroxyl $X_d$ can also be formed in situ from free hydroxyl, i.e. compounds containing free hydroxyl as $X_d$ can be reacted with suitable acylating agents, for example inorganic acid halides, such as phosphorus trichloride, phosphorus oxychloride or thionyl chloride, in suitable inert organic solvents, for example chloroform, or organic acid anhydrides or acid halides, such as acetic anhydride, phthalic anhydride, acetyl chloride or acetyl bromide, in the presence or preferably the absence of inert organic solvents or diluents, at a moderately elevated temperature up to the boiling point, in which case compounds of the general formula I in which $Y_1$ and $Y_2$ together are an additional bond are formed direct, whilst under milder conditions, with organic acid anhydrides or acid halides, starting materials of the general formula V in which $X_d$ is a corresponding acyloxy radical can be obtained.

In the starting materials of the general formula VII for process (e), the radical $X_e$ is, for example, a carboxyl group, and this can be replaced by hydrogen in a conventional manner, especially by heating to temperatures of about 220° to about 280° C. or even higher, if necessary in a stream of inert gas, for example a stream of nitrogen. If desired, the decarboxylation is carried out in the presence of an alkaline earth metal hydroxide, especially calcium oxide; however, it is also possible first to convert a carboxylic acid which falls under the general formula VII into an alkali metal salt or alkaline earth metal salt or, for example, also into a copper, mercury or silver salt, and to heat this salt, for example to the abovementioned temperatures.

Further radicals $X_e$ are, for example, hydroxyl and etherified hydroxyl, such as lower alkoxy, in particular methoxy or ethoxy, which, because of their benzyl position, can be replaced by hydrogen by means of hydrogenolysis. The hydrogenolysis can be carried out in a conventional manner, for example using the catalysts and solvents mentioned for process (b).

In the starting materials of the general formula VIII for process (f), a reactive esterified hydroxyl group $X_f$ is, for example, a hydroxyl group esterified by a strong acid, for example a mineral acid, such as a hydrogen halide acid, for example by hydriodic acid, hydrobromic acid or hydrochloric acid, or by an organic sulfonic acid, for example by benzenesulfonic acid, p-toluenesulfonic acid, p-bromobenzenesulfonic acid, methanesulfonic acid or ethanesulfonic acid.

The cyclisation which takes place with detaching of $HX_f$ can be effected in a conventional manner, for example by warming or moderate heating, for example up to 200°, using the dry material or, if necessary, in the presence of an inert solvent and/or in the presence of a condensing agent. For example, a basic condensing agent, such as a tertiary amine, for example triethylamine or pyridine, or an inorganic base, for example an alkali metal carbonate or hydroxide or alkaline earth metal carbonate or hydroxide, such as potassium hydroxide, is used when the starting materials are compounds in which $X_f$ is reactive esterified hydroxyl.

The starting materials of the general formula VIII, which in turn are novel, can be prepared in a manner known per se, for example by reacting corresponding compounds in which both symbols $X_f$ are reactive esterified hydroxyl groups, the preparation of which compounds is illustrated below, with compound of the general formula XII, which is given above, i.e. with lower alkylamines, lower alkenylamines, lower alkynylamines, cycloalkylamines or cycloalkyl-lower alkylamines. If desired, the compounds of the general formula VIII can be prepared in situ, i.e. in the same operation and using the same solvents and/or condensing agents as for the subsequent cyclisation.

The halogeno-magnesium or alkali metal radical $X_g$ present in one of the two reactants of the general formulae IX and X for process (g) is, for example, a chloromagnesium, bromo-magnesium, iodo-magnesium or lithium radical, and the halogen $X_g$ present in the other reactant is, for example, chlorine, bromine or iodine. The reactions according to process (f) can be carried out in a conventional manner, for example reactions with halogeno-magnesium compounds IX or X can be carried out in an inert solvent, such as an aliphatic ether, for example in diethyl ether, tetrahydrofuran or dioxan, and reactions with lithium compounds IX or X can be carried out, for example, in a hydrocarbon, such as hexane, benzene or toluene, if necessary in the presence of a catalytic agent, such as of a heavy metal salt, for example a halide, such as the chloride of copper, and/or at elevated temperature, for example at the boiling point of the reaction medium.

Those reactants of the general formula IX or X in which $X_g$ is an alkali metal radical or a halogeno-magnesium radical are preferably prepared in situ, for example by conventional reaction of the corresponding halogen compounds, which likewise fall under the general formula IX or X, with a reactive alkali metal compound, for example butyl-lithium, or with magensium, advantageously in a finely divided form in an inert solvent, such as an aliphatic ether, for example one of those mentioned above, and are advantageously subjected to further reaction without isolation.

Some starting materials of the general formula IX and X in which $X_g$ is halogen are known and others can be prepared analogously to the known compounds.

In the case of process (h), the formaldehyde is employed, for example, in oligomeric form, such as in the form of paraformaldehyde, or in the form of an aqueous solution, for example a 30–35% aqueous solution. The proton acid used is preferably a mineral acid, such as hydrochloric acid, especially concentrated hydrochloric acid, or sulfuric acid, especially moderately dilute, such as 66%, sulfuric acid. Based on the compounds of the general formula XII, the acids are employed in excess, i.e. in an amount of more than one equivalent and preferably of more than two equivalents. After initial cooling to control the exothermic reaction, the reaction temperature is preferably between 60° and 110° C. and especially 90°–100° C., a reaction time of, for example, about 1 to 10 hours being maintained.

A variant of process (h), which can be more advantageous, comprises first reacting a compound of the general formula XI with twice the molar amount of formaldehyde, for example in the form of an approximately 35% aqueous solution, and the equimolar amount of a mineral acid salt, especially the hydrochloride, of a compound of the general formula XII, or with the corresponding amount of a free compound of the general formula XII and the equinormal amount of mineral acid, and then converting the resulting crude reaction product to the desired end product, by gradually adding further mineral acid, such as concentrated sulfuric acid, with cooling, for example at 50°–70° C., and bringing the reaction to completion by heating to, for example, 90°–95° C.

In compounds of the general formula I in which $R_3$ is hydrogen, it is possible by conventional means, if desired, to introduce a radical $R_3$ which differs from hydrogen, for example by reaction with a reactive ester, preferably a halide or sulfonate, for example the chloride, bromide or iodide or benzenesulfonate, p-toluenesulfonate, p-bromobenzenesulfonate or methanesulfonate, of a lower alkanol, lower alkenol, lower alkynol or cycloalkyl-lower alkanol, or to introduce lower alkyl $R_3$ by reaction with a lower alkanol or di-lower alkyl ketone under reducing conditions, for example in the presence of hydrogen activated catalytically by noble metal catalysts, such as palladium, for example on charcoal, or platinum, or Raney nickel, the reactions being carried out, if necessary, in an inert solvent and/or under elevated pressure and/or at elevated temperature. A cycloalkyl-lower alkyl radical $R_3$ can also be introduced analogously. The analogous introduction of a cycloalkyl radical $R_3$ is also possible, but is less advantageous than the direct preparation of corresponding compounds of the general formula I, for example by process (a).

In the reaction of a compound of the general formula I in which the ring A is substituted by bromine and $R_3$ differs from hydrogen, or an analogous compound containing iodine in place of bromine, with a metal cyanide, the latter is, for example, copper-I cyanide and the reaction is carried out at elevated temperature, for example between about 130° C. and about 210° C., in an inert organic solvent with a corresponding boiling point or decomposition temperature, preferably in an amide or lactam, such as dimethylformamide—at temperatures of up to 140° C.—or 1-methyl-2-pyrrolidinone, or in sulfolane (tetrahydrothiophen 1,1-dioxide). Starting materials containing iodine in place of bromine in ring A can be prepared analogously to the compounds of the general formula I which contain bromine as a substituent of the ring A, using corresponding starting materials or precursors of such materials.

Suitable ether-splitting agents for the conversion of compounds of the general formula I in which the ring A is substituted by lower alkoxy, especially methoxy, to corresponding compounds containing hydroxyl in the same position are, for example, alkali metal cyanides, such as sodium cyanide, in oxidised dialkyl sulfides or their cyclic analogues, especially in dimethylsulfoxide or sulfolane, at elevated temperatures, for example at between about 150° and 200° C. The conversion of corresponding compounds containing substituted or unsubstituted benzyloxy, for example benzyloxy or p-lower alkoxybenzyloxy, such as p-methoxybenzyloxy, as a substituent of the ring A to corresponding compounds containing hydroxyl in the same position can be effected in an analogous manner, but under milder conditions, for example by treatment with concentrated hydrogen halide acids, if desired in the presence of acetic acid, at elevated temperatures, for example at temperatures between about 70° C. and the boiling point of the reaction mixture, or as a hydrogenolysis, by the action of hydrogen in the presence of a hydrogenation catalyst, for example platinum, palladium or Raney nickel, and, if desired, of hydrogen chloride, at room temperature and normal pressure or at moderately elevated temperatures and pressures in suitable organic solvents, for example methanol, ethanol or dioxan. The ether splitting, especially that of benzyl ethers, and in particular the hydrogenolysis of the latter, can also be effected together with the detaching of a corresponding radical $X_c$ according to process (c). Starting materials which contain a substituted or unsubstituted benzyloxy group as a substituent of the ring A can be prepared, for example, analogously to compounds of the general formula I containing lower alkoxy in the same position of the ring A, using corresponding starting materials or precursors thereof. However, it is also possible, in the manner indicated above, to split the methoxy group in 4-, 5-, 6- or 7-benzofurancarboxylic acids which are substituted by methoxy in the ring A and which arise in the reaction sequence described below for the preparation of starting materials of the general formula II, and, after forming corresponding lower alkyl esters if desired, to convert the hydroxyl group to the benzyloxy group in a known manner and to subject the resulting carboxylic acids or lower alkyl esters to further treatment analogously to the reaction sequence indicated below, i.e. first to reduce these to corresponding benzyloxy-benzofuranmethanols.

Starting materials of the general formula II in which $X_{a1}$ and/or $X_{a2}$ in the radical $R_3{}^a$ of the partial formula IIa are radicals replaceable by two hydrogen atoms, especially 2-piperidinones or glutarimides, can be prepared, for example, using 4-, 5-, 6- or 7-benzofurancarboxylic acids or their lower alkyl esters as starting materials. Some of these compounds are known, for example 2,3-dimethyl-6-benzofurancarboxylic acid, 2,3,7-trimethyl-6-benzofurancarboxylic acid, 2,3,5-trimethyl-6-benzofurancarboxylic acid, 2,3-dimethyl-4-benzofurancarboxylic acid, 2,3,7-trimethyl-4-benzofurancarboxylic acid and 2,3-dimethyl-5-benzofurancarboxylic acid, and also lower alkyl esters thereof, have been described by Y. Kawase and M. Takashima in Bull. Chem. Soc. Jap. 40, 1224–1231 (1967). Others are obtainable analogously to the known compounds, for example like the abovementioned carboxylic acids always substituted in the 2- and 3-position, from correspondingly substituted benzofurans, by acetylation by a Friedel-Crafts reaction and treatment of the acetyl compounds at 45° C. with aqueous sodium hypobromite solution, to which dioxan or tetrahydrofuran has been added. A further known method with diverse variants is, for example, the reaction of lower alkyl salicylates or lower alkyl m- or p-hydroxybenzoates, which can carry preferred substituents on the ring A, with α-halogeno-lower alkanals, -lower alkanones or -cycloalkanones in the presence of an acid-binding agent, such as potassium carbonate, and cyclisation of the resulting oxo-lower alkyl ether or oxo-cycloalkyl ether, for example by means of concentrated sulfuric acid in the cold. Oxo-lower alkyl ethers used for the cyclisation can also be prepared from the lower alkyl hydroxybenzoates in two stages, i.e. by reacting the said esters with 2-lower alkynyl halides and hydrating the resulting lower alkynyl ethers in a conventional manner, for example by treatment with mercury-II sulfate in aqueous-lower alkanolic solution at a slightly elevated temperature.

A process which is likewise suitable for the preparation of those benzofurancarboxylic acids of the desired type in which at least the 2-position, and preferably also the 3-position, is substituted, i.e. $R_1$ or $R_1$ and $R_2$ differ from hydrogen and together are, for example, the tetramethylene radical, is the metalation, described by H. Gilman et al., J. Am. Chem. Soc. 57, 2095–2099 (1935) for the preparation of 6,7,8,9-tetrahydro-dibenzofuran-4-carboxylic acid, of the correspondingly substituted benzofuran, for example with phenyl-lithium in ether, reaction of the metal compound with carbon dioxide and, if desired, subsequent esterification by conventional methods.

The resulting lower alkyl 4-, 5-, 6- or 7-benzofurancarboxylates, which may be substituted according to the definitions of $R_1$ and $R_2$ and in the ring A, or the free carboxylic acids are reduced to the corresponding 4-, 5-, 6- or 7-benzofuranmethanols, for example by means of complex hydrides, such as lithium aluminium hydride, in ether-like solvents, such as tetrahydrofuran, and the methanols are converted into the corresponding 4-, 5-, 6- or 7-benzofurancarboxaldehydes by partial oxidation, for example by means of manganese dioxide in an inert organic solvent, such as toluene. Individual representatives of these aldehydes are likewise known, for example the compounds 2,3-dimethyl-4-methoxy-7-benzofurancarboxaldehyde, 2,3-dimethyl-5-methoxy-6-benzofurancarboxaldehyde, 2,3-dimethyl-6-methoxy-5-benzofurancarboxaldehyde and 2,3-dimethyl-7-methoxy-6-benzofurancarboxaldehyde, which are prepared by the formylation by means of dimethylformamide and phosphorus oxychloride, in accordance with the method of Vilsmeier which can be used for compounds containing radicals $R_1$ which differ from hydrogen [c.f. R. Royer et al., Bull. Soc. Chim. France 1965, 2607–2616], and 2,3-dimethyl-7-benzofurancarboxaldehyde, which is obtained by cyclising 2-(1-methyl-2-oxopropoxy)-benzaldehyde [c.f. C. Goldenberg et al., Chim. Thérap. 1966, 221–227], and also some benzofurancarboxaldehydes which are unsubstituted in the 2-position, such as, for example, 5-benzofurancarboxaldehyde, and are obtainable by decarboxylation of corresponding unsubstituted or further substituted formyl-2-benzofurancarboxylic acids [c.f. C. Goldenberg et al., loc. cit.], and 6-methoxy-5-benzofurancarboxaldehyde [c.f. P. Quevel and E. Bisagni, Eur. J. Med. Chem. 9, 335–340 (1974)]. 2-Piperidinones which fall under the general formula II can be obtained from the substituted or unsubstituted 4-, 5-, 6- or 7-benzofurancarboxaldehydes, for example by first preparing appropriately substituted 4-, 5-, 6- or 7-benzofuranacrylonitriles by reaction with diethoxyphosphonoacetonitrile in the presence of bases or by condensation with cyanoacetic acid in the presence of piperidine in glacial acetic acid at elevated temperatures, adding a di-lower alkylmalonate onto these nitriles in a manner which is in itself known, then hydrogenating the cyano group in the addition product catalytically, for example in the presence of Raney nickel under elevated pressure and at elevated temperature in a lower alkanol, whereupon the corresponding lower alkyl 4-(4-, 5-, 6- or 7-benzofuranyl)-2-oxonipecotinate is formed, under lactamisation, and can be hydrolysed in a conventional manner to give the free acid, which can be decarboxylated, also in a conventional manner, for example by boiling in toluene, to give the desired 2-piperidinone of the general formula II. The abovementioned lower alkyl 2-oxonipecotinates substituted in the 4-position can also be converted into the desired 2-piperidinones in one stage by a reaction analogous to one described by A. P. Krapcho et al., Tetrahedron Letters 1973, 957, by heating with sodium chloride and water in dimethylsulfoxide.

The 2,6-piperidinediones falling under the general formula II can be obtained starting from the abovementioned 4-, 5-, 6- or 7-benzofurancarboxaldehydes, which may be substituted according to the definition of $R_1$ and $R_2$ and in the ring A, by first subjecting these aldehydes to a condensation reaction with twice the molar amount of a lower alkylacetoacetate in an appropriate lower alkanol, for example in accordance with the method of Knoevenagel, using piperidine as the condensing agent, whereupon the corresponding di-lower alkyl 2-(4-, 5-, 6- or 7-benzofuranyl)-4-hydroxy-4-methyl-6-oxo-1,3-cyclohexanedicarboxylates are formed, a keto group simultaneously being reacted with a methyl group. From these esters, the corresponding 3-(4-, 5-, 6- or 7-benzofuranyl)-glutaric acids are obtained by alkaline hydrolysis, for example by boiling in aqueous-lower alkanolic alkali metal hydroxide solution, and from these acids the corresponding anhydrides can be obtained in a conventional manner, for example by boiling in acetic anhydride, and from the anhydrides, the glutarimides or 2,6-piperidinediones falling under the general formula II are obtained, likewise in a conventional manner, by reaction with ammonia or amines of the general formula XII, for example by heating with ammonium acetate or boiling with an amine of the general formula XII in the presence of glacial acetic acid, or with the corresponding acetate in an inert organic solvent, for example toluene, the water formed preferably being separated off.

Starting materials of the general formulae III and V and some of the starting materials of the general formulae IV and VII can be obtained, for example, starting from compounds of the general formula IX in which $X_g$ is halogen, in particular bromine, $R_1$ and $R_2$ are as defined under formula I and the ring A is not further substituted or is further substituted. Some representatives of these compounds are known, and others can be prepared analogously to the known representatives, for example by cyclising (bromophenoxy)-alkanones or acetals of α-(bromophenoxy)-alkanals, for example with concentrated sulfuric acid, as in the case of 7-bromo- 2,3-dimethylbenzofuran [c.f. Bull. Soc. Chim. France 1966, 586–594], by cyclising esters of 2-(2,3-dibromopropyl)-bromophenols, for example with potassium hydroxide, as in the case of 2-methyl-5-bromobenzofuran [c.f. R. Adams et al., J. Am. Chem. Soc. 41, 659, 661 (1919) and L. Claisen, Ber. 53, 322–325 (920)] or, if desired, also by direct bromination, as in the case of 4-bromo-5-methoxybenzofuran [c.f. D. S. Noyce and R. W. Nichols, J. Org. Chem. 37, 4313 (1972)] or by cyclising bromine-substituted 2-formylphenoxyacetic acids by boiling with sodium acetate in acetic anhydride/acetic acid, for example as in the case of 5-bromo-6-methoxybenzofuran from (4-bromo-2-formyl-5-methoxyphenoxy)-acetic acid [c.f. L. R. Worden et al., J. Org. Chem. 34, 2311–2313 (1969)]. The compounds of the general formula IX in which $X_g$ is halogen, in particular bromine, are first converted, as indicated in the case of process (g), into corresponding compounds with a halogeno-magnesium radical or alkali metal radical $X_g$, in particular a bromo-magnesium radical or lithium radical $X_g$, and these organometallic compounds are reacted in situ with 4-piperidinones which contain, in the 1-position, a radical corresponding to the definition of $R_3$, with the exception of hydrogen, by a process analogous to process (g), to give compounds of the general formula V which contain hydroxyl as the radical $X_d$ and also are starting materials for process (e) having the general formula VII in which hydroxyl is the detachable radical $X_e$. Acylation of such hydroxy compounds under mild conditions, for example with a lower alkanoyl halide, such as acetyl chloride, in the presence of pyridine in the cold gives corresponding compounds of the general formula V with an acyloxy radical, for example the acetoxy radical, as the radical $X_d$. Dehydration or detachment of acid from the compounds of the general formula V according to process (d) gives compounds of the general formula I in which $Y_1$ and $Y_2$ are an additional bond, and which at the same time are starting materials of the general formula III for process (b).

Starting materials of the general formula III in which $R_4{}^b$ is a 4-pyridyl radical or a corresponding quaternary radical which is substituted in the 1-position by a radical $R_3$ which differs from hydrogen are obtained, for example, by reacting the abovementioned compounds of the general formula IX in which the radical $X_g$ is halogen, in particular bromine, with a 4-metal-pyridine, for example with 4-lithium-pyridine, and, if desired, by subsequently quaternising the product with a lower alkyl halide, lower alkenyl halide, lower alkynyl halide or cycloalkyl-lower alkyl halide.

Starting materials of the general formula IV in which Ac is the acyl radical of a carbonic acid half-ester or thiocarbonic acid half-ester or is a cyano radical or a chlorocarbonyl radical can be prepared, for example, from corresponding compounds of the general formula I in which $R_3$ is an easily detachable group, such as the allyl group and in particular the methyl group, by reaction with chloroformates or chlorothioformates, in particular with ethyl chloroformate, tert.-butyl chloroformate, benzyl chloroformate, phenyl chloroformate or S-methyl chlorothioformate, or with cyanogen bromide or phosgene in an inert organic solvent at elevated temperature, for example in toluene at the boiling point thereof.

It is also possible, for example, to use carboxylic acid halides, for example acetyl bromide or benzoyl chloride, in place of the abovementioned carbonic acid derivatives, but the corrresponding reaction to detach the $R_3$ group usually requires more energetic conditions and is less complete than, for example, when ethyl chloroformate or, in particular, cyanogen bromide is used.

Other starting materials of the general formula IV can be prepared, for example, by reacting abovementioned compounds of the general formula IX in which $X_g$ is a halogeno-magnesium radical or alkali metal radical, in particular a lithium radical, with 4-piperidinones which contain, in the 1-position, a radical which can be detached by reduction or solvolysis, for example the benzyl radical, the benzyloxycarbonyl radical or an acyl radical.

Starting materials of the general formula VII in which $X_e$ is a carboxyl group are obtained, for example, by condensation of a 4-, 5-, 6- or 7-benzofuranacetonitrile, which may be substituted according to the definition for $R_1$ and $R_2$ and in the ring A, with a N,N-bis-(2-halogenoethyl)-lower alkylamine, -lower alkenylamine, -lower alkynylamine, -cycloalkylamine or -cycloalkyl-lower alkylamine in the presence of an alkaline condensing agent, for example sodium amide or lithium amide or sodium hydride, followed by hydrolysis or solvolysis of the resulting 4-(benzofuranyl)-isonipecotinonitrile, substituted in the 1-position by a substituent $R_3$ which differs from hydrogen, to give the corresponding carboxylic acid, if necessary via the conventional intermediates, that is to say the imide chloride hydrochloride, imido-lower alkyl ester and lower alkyl ester. If suitable N,N-bis-(2-halogenoethylamides, for example N,N-bis-(2-chloroethyl)-p-toluenesulfonamide, are used for this reaction sequence in place of the abovementioned N,N-bis-(2-halogenoethyl) compounds, hydrolysis or solvolysis of the nitrile group and subsequent decarboxylation analogous to process (e) gives starting materials of the general formula IV for process (c).

Starting materials of the general formula VIII for the cyclisation according to process (f) are obtained, for example, by reducing the di-lower alkyl 3-(4-, 5-, 6- or 7-benzofuranyl)-glutarates, or the free acids, already mentioned as intermediates for the preparation of starting materials of the general formula II by means of hydrides, for example lithium aluminium hydride or diborane, reacting the 1,5-pentanediols formed, which are correspondingly substituted in the 3-position, with inorganic acid halides, for example thionyl chloride or phosphorus tribromide, to give 1,5-dihalogenopentanes which are correspondingly substituted in the 3-position, or with organic sulfonic acid halides, such as methanesulfonyl chloride or p-toluenesulfonyl chloride, to give corresponding 1,5-bis-(sulfonyloxy)-pentanes substituted in the 3-position, and reacting these compounds with amines of the general formula XII, preferably in situ, i.e. immediately before the cyclisation according to process (f), in the solvent envisaged for this reaction.

Starting materials of the general formula XI can again be prepared from the compounds of the general formula IX, which have already been mentioned and some of which are known, in which $X_g$ is a halogen atom, in particular bromine, and $R_1$ and $R_2$ are as defined under formula I and the ring A is not further substituted or is further substituted, by converting these compounds into the corresponding halogeno-magnesium compounds or alkali metal compounds, which likewise fall under the general formula IX, and reacting these with acetone and dehydrating the initially formed tertiary hydroxy compounds under the conventional conditions of Grignard reactions or alkali metal-organic reactions. The reaction of 4-, 5-, 6- or 7-acetylbenzofurans which are preferably substituted in the 2-position and 3-position, for example those described in the abovementioned Bull. Chem. Soc. Japan 40, 1224–1231 (1967), with methyl-magnesium halides and again dehydration of the tertiary hydroxy compounds initially formed is also possible.

Some starting materials of the general formula X are known, for example 4-chloro-1-methylpiperidine [McElvain, Rorig, J. Am. Chem. Soc. 70, 1826 (1948)] and 1-ethyl-4-chloropiperidine [Paul, Tchelitcheff, Bull. Soc. Chim. France, 1954, 982, 983], and others can be prepared analogously to the known compounds. The starting materials of the general formula XII need no further explanation.

The starting materials used for carrying out the reactions according to the invention are preferably those which result in the groups of end products which have been mentioned in particular initially and especially which result in the end products specifically described or singled out.

Depending on the process conditions and starting materials, the compounds of the general formula I are obtained in the free form or in the form of their acid addition salts, which are also included in the invention. Thus, for example, basic, neutral or mixed salts and in some cases also hemihydrates, monohydrates, sesquihydrates or polyhydrates thereof can be obtained. The acid addition salts of the novel compounds can be converted into the free bases in a manner known per se, for example using basic agents, such as alkalis or ion exchangers. On the other hand, if desired, resulting free bases can be converted into acid addition salts using organic or inorganic acids. Acids which are suitable for the formation of pharmaceutically acceptable salts are used, in particular, for the preparation of these acid addition salts. Examples of such acids are: hydrogen halide acids, sulfuric acids, phosphoric acids, nitric acid, perchloric acid, aliphatic, alicyclic, aromatic or heterocyclic carboxylic or sulfonic acids, such as formic acid, acetic acid, propionic acid, succinic acid, glycolic acid, lactic acid, malic acid, tartaric acid, citric acid, maleic acid, hydroxymaleic acid, pyruvic acid, phenylacetic acid, benzoic acid, p-aminobenzoic acid, anthranilic acid, p-hydroxybenzoic acid, salicyclic acid, p-aminosalicylic acid, embonic acid, methanesulfonic acid, ethanesulfonic acid, hydroxyethanesulfonic acid, ethylenesulfonic acid, halogenobenzenesulfonic acid, toluenesulfonic acid or naphthalenesulfonic acid, sulfanilic acid or other acid substances, such as ascorbic acid.

These and, if they can readily be crystallised, other salts can also be used for purifying the novel compounds, for example by converting the free compounds into their salts, isolating the salts and converting them into the free compounds again. Because of the close relationship between the novel compounds in the free form and in the form of their salts, what is stated in this specification in respect of the free compounds also applies by analogy to the corresponding salts.

Depending on the choice of starting materials and procedures, the novel compounds can be in the form of optical antipodes or racemates, or, if they contain at least two asymmetric carbon atoms, also in the form of racemate mixtures or in some cases also as mixtures of position isomers.

Racemate mixtures obtained can be separated into the two stereoisomeric (diastereomeric) racemates in a known manner, for example by chromatography and/or fractional crystallisation, on the basis of the physicochemical differences of the diastereomers. Mixtures of position isomers can likewise be separated, preferably by fractional crystallisation.

Resulting racemates can be separated into the antipodes by methods known per se, for example by recrystallisation from an optically active solvent, by treatment with suitable micro-organisms or by reaction with an optically active substance which forms a salt with a racemic compound, in particular an acid, and separation of the salt mixture thus obtained, for example on the basis of different solubilities, into the diastereomeric salts, from which the free antipodes can be liberated by the action of suitable agents. Particularly useful optically active acids are, for example, the D- and L-forms of tartaric acid, O,O-di-p-toluoyltartaric acid, malic acid, mandelic acid, camphorsulfonic acid, glutamic acid, aspartic acid or quinic acid. The more active of the two antipods is advantageously isolated.

The invention also relates to those embodiments of the process according to which a compound obtainable as an intermediate at any stage is used as the starting material and the missing process steps are carried out or the process is discontinued at any stage, or according to which a starting material is formed under the reaction conditions, or in which a reaction component is used, if desired, in the form of a derivative, for example a salt.

The compounds of the general formula I and their pharmaceutically acceptable acid addition salts are administered in the form of pharmaceutical preparations, preferably perorally or rectally, but they can also be administered parenterally in the form of aqueous solutions of their acid addition salts.

The daily doses for warm-blooded animals vary between 0.03 and 3 mg/kg, and are preferably between 2.5 and 50 mg for warm-blooded animals with a body weight of about 70 kg. Suitable dosage forms, such as coated tablets, tablets or suppositories, preferably contain 1 to 25 mg of an active ingredient of the invention, that is to say of a compound of the general formula I or of a pharmaceutically acceptable acid addition salt thereof. To produce pharmaceutical preparations according to the invention, the active ingredient is combined with at least one pharmaceutical carrier. To produce the abovementioned dosage forms which can be administered orally, the active ingredient is processed, for example, with solid, powdery carriers, such as lactose, sucrose, sorbitol, mannitol, starches, such as potato starch, corn starch or amylopectin, and furthermore laminaria powder or citrus pulp powder, cellulose derivatives or gelatine, with or without the addition of lubricants, such as magnesium or calcium stearate or polyethylene glycols, to give tablets or coated tablet cores. The latter are coated, for example, with concentrated sugar solutions, which can additionally contain, for example, gum arabic, talc and/or titanium dioxide, or with a lacquer which is dissolved in readily volatile organic solvents or solvent mixtures. Colorants can be added to these coatings, for example to distinguish different dosages of active ingredients. Further suitable oral dosage forms are hard gelatine capsules and soft, closed gelatine capsules which are plasticised with glycerol. The hard gelatine capsules preferably contain the active ingredient in granulate form, in admixture with lubricants, such as talc or magnesium stearate, and optionally stabilisers, such as sodium meta-bisulfite or ascorbic acid.

Suitable dosage forms for rectal administration are, for example, suppositories, which consist of a combination of an active ingredient with a suppository base. Examples of suitable suppository bases are natural or synthetic triglycerides, paraffin hydrocarbons, polyethylene glycols or higher alcohols. Gelatine rectal capsules, which consist of a combination of the active ingredient with a base material, are also suitable. Suitable base materials are, for example, liquid triglycerides, polyethylene glycols or paraffin hydrocarbons.

Ampoules for parenteral, in particular intramuscular, administration contain preferably a watersoluble salt of an active ingredient in a concentration of preferably 0.5–5%, optionally together with suitable stabilisers and buffer substances, in aqueous solution.

The following directions will serve to illustrate the preparation of tablets, sugar-coated tablets, suppositories and ampoules in more detail:

(a) 100.0 g of 4-(2,3-dimethyl-5-benzofuranyl)-piperidine hydrochloride are mixed with 450 g of lactose and 292 g of potato starch and the mixture is moistened with an alcoholic solution of 8 g of gelatine and granulated through a sieve. After the moist granulate has dried, it is mixed with 60 g of potato starch, 60 g of talc, 10 g of magnesium stearate and 20 g of highly disperse silica, and the mixture is compressed to 10,000 tablets each weighing 100 mg and containing 10 mg of active ingredient, and if desired, the tablets can be provided with breaking grooves for finer adjustment of the dosage.

(b) 12.5 g of 4-(2,3-dimethyl-6-benzofuranyl)-piperidine hydrochloride are thoroughly mixed with 16 g of corn starch and 16 g of highly disperse silica. The mixture is moistened with a solution of 2 g of stearic acid, 6 g of ethyl cellulose and 6 g of stearine in approx. 70 ml of isopropyl alcohol and granulated through a sieve of 1.2 mm mesh width. The granulate is dried for approx. 14 hours and then forced through a sieve of 1.2 to 1.5 mm mesh width. Thereafter, it is mixed with 16 g of corn starch, 16 g of talc and 2 g of magnesium stearate and the mixture is compressed to 1,000 coated tablet cores. These are coated with a concentrated syrup of 2 g of shellac, 7.5 g of gum arabic, 0.15 g of colorant, 2 g of highly disperse silica, 25 g of talc and 55.35 g of sugar and the coating is dried. The resulting coated tablets each weigh 158.5 mg and each contains 12.5 mg of active ingredient.

(c) 25.0 g of 4-(6,7,8,9-tetrahydro-2-dibenzofuranyl)-piperidine hydrochloride and 1,975 g of a finely ground suppository base (for example cacao butter) are thoroughly mixed and the mixture is then melted. 1,000 suppositories of 2 g are cast from the melt, which is kept homogeneous by stirring. Each suppository contains 25 mg of active ingredient.

(d) 12.5 g of 4-(2,3-dimethyl-5-benzofuranyl)-piperidine hydrochloride are dissolved in 1 litre of doubly distilled water which is free from pyrogens and the solution is filled into 1,000 ampoules and sterilised. One ampoule contains a 2.5% solution of 12.5 mg of active ingredient.

The following examples illustrate in more detail the preparation of the novel compounds of the general formula I and of starting materials which were hitherto unknown, without in any way restricting the scope of the invention. The temperatures given are in degrees Centigrade.

EXAMPLE 1

6.1 g (0.025 mol) of 4-(2,3-dimethyl-5-benzofuranyl)-2-piperidinone, partly dissolved or suspended in 50 ml of absolute tetrahydrofuran, are slowly added dropwise to a suspension, cooled in an ice-water bath and under nitrogen, of 2.8 g (0.075 mol) of lithium aluminium hydride in 50 ml of absolute tetrahydrofuran in the course of about 15 minutes, with stirring. Vigorous foaming and a rise in temperature to about 20° are observed during this addition. When the addition has ended, the cooling bath is removed and the grey reaction mixture is refluxed for 6 hours. Thereafter, the reaction mixture is cooled in an ice-water bath and excess reducing agent is decomposed carefully with 8.4 ml of water and 5.6 ml of 2 N sodium hydroxide solution. The complex thereby formed is stirred for a further 15 minutes and then filtered off with suction and the residue is washed twice with about 20 ml of absolute tetrahydrofuran. The filtrate is evaporated completely in a rotary evaporator on a waterbath.

The resulting crude product is taken up in about 15 ml of methanol and the pH value is adjusted to 3 with approximately 6 N methanolic hydrochloric acid. The crude hydrochloride is then precipitated by adding ether. The hydrochloride is filtered off with suction, washed with ethanol/ether (1:9) and dried. After recrystallisation from methanol/ether, the 4-(2,3-dimethyl-5-benzofuranyl)-piperidine hydrochloride thus obtained melts at 269°–270°.

The starting material is prepared as follows:

(a) 21.8 g (0.1 mol) of ethyl 2,3-dimethyl-5-benzofurancarboxylate [prepared according to the method of Y. Kawase and M. Takashima, Bull. Chem. Soc. Japan 40, 1224 (1967)] are dissolved in 50 ml of anhydrous tetrahydrofuran. This solution is added dropwise to a suspension, cooled with ice-water, of 3.8 g (0.1 mol) of lithium aluminium hydride in 150 ml of anhydrous tetrahydrofuran, with stirring. The reaction mixture is stirred at 0° for 2 hours; it is then allowed to warm to room temperature. The resulting suspension is cooled with an ice-water mixture and excess reducing agent is decomposed by adding 11.4 ml of water and 7.6 ml of 2 N sodium hydroxide solution dropwise. The suspension of a white complex thereby formed is stirred for a further 15 minutes, and the complex is then filtered off with suction and washed twice with about 50 ml of tetrahydrofuran each time. The combined filtrates are evaporated to dryness in a rotary evaporator on a water bath. The colourless oil thereby obtained crystallises completely when left to stand, and the crude product has a melting point of 70°–71°. The purity thereof is adequate for its direct further use.

(b) A solution of 158.2 g (0.9 mol) of 2,3-dimethyl-5-benzofuranmethanol in 1,500 ml of toluene is stirred with 400 g of manganese dioxide at room temperature for 3 days. Thereafter, the oxidising agent is filtered off over diatomaceous earth, the material on the filter is washed with toluene and the filtrate is evaporated completely in a rotary evaporator. The pale yellowish residue of 2,3-dimethyl-5-benzofurancarboxaldehyde crystallises spontaneously and has a melting point of 80°–81°. A sample recrystallised from hexane melts at 81°–82°. The product can be used further without purification.

(c) A solution of 52.2 g (0.3 mol) of 2,3-dimethyl-5-benzofurancarboxaldehyde and 55.8 g (0.315 mol) of diethoxyphosphonacetronitrile in 50 ml of methylene chloride is added dropwise to an emulsion consisting of 300 ml of methylene chloride, 170 ml of 50% sodium hydroxide solution and 11 g of a 40% aqueous solution of tetrabutylammonium hydroxide at room temperature in the course of 30 minutes, with vigorous stirring. The reaction mixture warms to about 35° by itself. When the addition has ended, the reaction mixture is stirred at room temperature for 60 minutes and then poured onto 200 ml of water, the organic layer is separated off and the aqueous phase is extracted twice more with methylene chloride. The combined methylene chloride phases were washed three times with saturated sodium chloride solution dried over magnesium sulfate and concentrated in a rotary evaporator. During this concentration, spontaneous crystallisation starts at a total volume of about 100 ml. After 100 ml of hexane are therefore also added, the mixture is allowed to crystallise further and the crystals of 2,3-dimethyl-5-benzofurancrylonitrile formed are then filtered off with suction. Still further pure substance can be obtained by crystallising the mother liquor several times. Most of the product obtained consists of the trans-isomer. The fourth crystal fraction contains about 50% of cis-isomer, as can be concluded from the nuclear magnetic resonance spectrum. The mother liquor from the fourth crystallisation likewise consists of a mixture of the cis-isomer and trans-isomer in a ratio of about 1:1. The presence of the cis-isomer does not interfere with the further course of the reaction.

(d) 3.5 g (0.15 mol) of small pieces of sodium are added in portions to a solution of 30.0 g (0.15 mol) of 2,3-dimethyl-5-benzofurancrylonitrile and 24.8 g (0.155 mol) of dry diethyl melonate in 70 ml of absolute ethanol. The reaction mixture boils as a result of the exothermic reaction. When the addition has ended (after about 15 minutes), the yellow reaction mixture is refluxed for a further 60 minutes. The reaction mixture is then cooled, and 9 ml (1 equivalent) of glacial acetic acid and 100 ml of water are added. The resulting mixture is poured onto 1 liter of ether, 400 ml of saturated sodium chloride solution are added and the organic phase is separated off. The aqueous phase is then extracted twice more with 400 ml of ether each time. The organic phases are washed three times with saturated sodium chloride solution, once with aqueous 1 N potassium bicarbonate solution and again with saturated sodium chloride solution. The organic phases are then combined, dried over magnesium sulfate and evaporated in a rotary evaporator. The oil which remains crystallises gradually. It is taken up in 80 ml of hot isopropanol, and about 150 ml of ligroin are added at elevated temperature. Diethyl [2-cyano-1-(2,3-dimethyl-5-benzofuranyl)-ethyl]-malonate of melting point 84°–86° crystallises out of the solution when the solution is cooled slowly. Still further crystallised substance can be obtained analogously from the mother liquor. A sample of the first crystals melts at 86.5°–87° when recrystallised from isopropanol/ligroin.

(e) A solution of 35.7 g of diethyl [2-cyano-1-(2,3-dimethyl-5-benzofuranyl)-ethyl]-malonate in 180 ml of absolute ethanol is hydrogenated at 70°–80° in the presence of 8 g of Raney nickel under an initial pressure of 120 bars for 13 hours. Thereafter, the catalyst is filtered off over diatomaceous earth and the filtrate is evaporated completely in a rotary evaporator on a water bath. Purification of the crude ethyl 4-(2,3-dimethyl-5-benzofuranyl)-2-oxo-nipecotinate, which crystallises slowly, is dispensed with because of the difficulties which occur during crystallisation as a result of the diastereomer mixture present. The crude product is therefore used further without additional purification. In a thin layer chromatogram on silica gel using the running agent chloroform+2% methanol, the main spot is visible at a Rf value of about 0.2 (iodine) and 3 weak secondary spots can be seen at Rf values of 0.15, 0.3 and 0.7.

(f) 50 ml of 2 N sodium carbonate solution and 50 ml of 2 N sodium hydroxide solution are added to a solution of 31.5 g (0.1 mol) of ethyl-4-(2,3-dimethyl-5-benzofuranyl)-2-oxo-nipecotinate in 100 ml of ethanol. Thereafter, the reaction mixture is warmed and refluxed for 30 minutes. The reaction mixture is then cooled and 2 N hydrochloric acid is added until the pH value is about 4. A crystalline precipitate thereby separates out and is filtered off with suction, washed with cold water and then dried. The resulting 4-(2,3-dimethyl-2-benzofuranyl)-2-oxo-nipecotinic acid can be used further without purification.

(g) A suspension of 28.7 g (0.1 mol) of 4-(2,3-dimethyl-5-benzofuranyl)-2-oxo-nipecotinic acid in 120 ml of toluene is heated gradually to the boil, under reflux. At an internal temperature of about 100°, evolution of carbon dioxide and successive solution of the suspended substance takes place. After about 10 minutes, no further evolution of gas is observed. The yellow solution formed is refluxed for a further 20 minutes and then cooled, whereupon a crystalline precipitate gradually separates out. 200 ml of hexane are added in order to bring the crystallisation to completion. The crystals are then filtered off with suction and washed with toluene. The resulting 4-(2,3-dimethyl-5-benzofuranyl)-2-piperidinone melts at 168°–170°. Still further crude product is obtained from the mother liquor by crystallisation from ethyl acetate/hexane. A sample recrystallised from ethyl acetate/hexane melts at 172.5°–173.5°. The crude product is sufficiently pure for further use.

EXAMPLE 2

0.95 g (0.025 mol) of lithium aluminium hydride is suspended in 10 ml of absolute tetrahydrofuran. 5.14 g (0.02 mol) of 1-methyl-4-(2,3-dimethyl-5-benzofuranyl)-2-piperidinone, dissolved in 40 ml of absolute tetrahydrofuran, are added dropwise to this suspension in the course of 20 minutes, whilst cooling with an ice-water mixture. The mixture is stirred at 0°–5° for 30 minutes and is then allowed to warm to room temperature. After a reaction time of 30 minutes at room temperature, the reaction mixture is cooled and excess reducing agent is destroyed with 3 ml of water and 2 ml of 2 N sodium hydroxide solution, whilst cooling with ice-water. The suspension formed is stirred for 15 minutes and then filtered with suction and the material on the filter is washed with tetrahydrofuran. The filtrate is evaporated completely in a rotary evaporator. The yellow, clear, oily residue is taken up in absolute ethanol, the ethanol mixture is acidified to a pH value of 4 with approximately 6 N ethereal hydrochloric acid and the crude hydrochloride is precipitated by adding ether. The 1-methyl-4-(2,3-dimethyl-5-benzofuranyl)-piperidine hydrochloride thus obtained melts at 236°–238°. A sample recrystallised from ethanol/ether melts at 240°–242°.

The starting material is prepared as follows:

(a) 1.15 g (0.024 mol) of a 50% suspension of sodium hydride in mineral oil are washed three times with about 20 ml of pentane each time, until free from oil. 15 ml of absolute dimethylsulfoxide are added to the sodium hydride which remains, at room temperature and under nitrogen. A solution of 4.6 g (0.02 mol) of 4-(2,3-dimethyl-5-benzofuranyl)-2-piperidinone [c.f. Example (1a) to (g)] in 20 ml of dimethylsulfoxide is dripped into the solution of sodium dimethylsulfoxide at room temperature in the course of about 15 minutes, whereupon a brownish suspension is formed, with frothing. 3.4 g (0.024 mol) of methyl iodide are added dropwise to this suspension at room temperature and the mixture is then stirred at room temperature for a further 90 minutes. The reaction mixture is then poured onto about 150 ml of water and extracted three times with ether. The organic phases are washed several times with water and then with saturated sodium chloride solution and are combined, dried over magnesium sulfate and evaporated in a rotary evaporator. The 1-methyl-4-(2,3-dimethyl-5-benzofuranyl)-2-piperidinone which remains, in the form of yellowish ice-like crystals, melts at 142°–144°. This product is of sufficient purity and can be used directly for the subsequent reduction.

EXAMPLE 3

4-(2,3-Dimethyl-6-benzofuranyl)-piperidine hydrochloride of melting point 275°–277° (from methanol/ether) is obtained analogously to Example 1 by reducing 6.1 g (0.025 mol) of 4-(2,3-dimethyl-6-benzofuranyl-2-piperidinone.

The staring material is prepared as follows:

(a) 2,3-Dimethyl-6-benzofuranmethanol of melting point 85°–85.5° (from ether/hexane) is obtained analogously to Example (1a) by reducing 21.8 g (0.1 mol) of ethyl 2,3-dimethyl-6-benzofurancarboxylate [prepared in accordance with the method of Y. Kawase and M. Takashima, Bull. Chem. Soc., Japan 40, 1224 (1967)].

(b) 2,3-Dimethyl-6-benzofurancarboxaldehyde of melting point 73°–74° (from hexane) is obtained analogously to Example 1b) by oxidising 158.2 g (0.9 mol) of 2,3-dimethyl-6-benzofuranmethanol.

(c) 2,3-Dimethyl-6-benzofuranacrylonitrile is prepared from 52.2 g (0.3 mol) of 2,3-dimethyl-6-benzofurancarboxaldehyde in a manner analogous to that described in Example (1c). The reaction product consists of a cis/trans mixture in a ratio of 3:7, the melting point (from isopropanol) of the pure isomers being 125°–128° for the cis-isomer and 134°–136°0 for the trans-isomer.

(d) Diethyl[2-cyano-1-(2,3-dimethyl-6-benzofuranyl)ethyl]-malonate is prepared in a manner analogous to that described in Example 1d), starting from 30.0 g (0.15 mol) of 2,3-dimethyl-6-benzofuranacrylonitrile. The melting point of a sample which, according to the thin layer chromatogram, is a single compound, is 118°–120° (from isopropanol/hexane). Samples which are less pure but are suitable for further use have melting points between 110° and 120°.

(e) Ethyl 3-(2,3-dimethyl-6-benzofuranyl)-2-oxonipecotinate is prepared from 35.7 g (0.1 mol) of diethyl [2-cyano-1-(2,3-dimethyl-6-benzofuranyl)ethyl]-malonate in a manner analogous to that described in Example 1e), but at a reaction temperature of 90°–100°. The pure substance melts at 157°–159° (from methylene chloride/hexane). Deviations in the melting point to a lower value are to be attributed to different proportions of the diastereomers in the crystals.

(f) A solution of 3.15 g (0.01 mol) of ethyl 4-(2,3-dimethyl-6-benzofuranyl)-2-oxonipecotinate, 0.64 g (0.011 mol) of sodium chloride and 0.36 ml (0.02 mol) of water in 10 ml of dimethylsulfoxide is heated to 150° C. for 3¼ hours. The solution becomes pale brownish in colour and carbon dioxide is evolved. The reaction mixture is then cooled, poured onto about 50 ml of water and extracted with methylene chloride. The organic phase is washed several times with water and then dried over sodium sulfate and evaporated completely in a rotary evaporator. 4-(2,3-Dimethyl-6-benzofuranyl)-2-piperidinone is obtained as pale yellowish crystals of melting point 195°–197°, the purity of which is sufficient for direct further use. A sample recrystallised from ethyl acetate melts at 200°–201°.

EXAMPLE 4

2.57 g (0.010 mol) of 3-(2,3-dimethyl-5-benzofuranyl)-glutarimide are added in portions to a suspension of 0.76 g (0.020 mol) of lithium aluminium hydride in 100 ml of ether, whilst cooling in an ice-water bath. When the addition has ended, the reaction mixture is allowed to warm to room temperature and is then refluxed for 2 hours. The resulting sand-coloured suspension is cooled in an ice-water bath, 1.52 ml of 2 N sodium hydroxide solution and 2.2 ml of water are successively added slowly and the white suspension is stirred at the above temperature for 30 minutes. The reaction mixture is then filtered and the residue on the filter is washed several times with methylene chloride. The combined filtrates are evaporated in a rotary evaporator and the residue is dissolved in ethanol. 4(2,3-Dimethyl-5-benzofuranyl)-piperidine hydrochloride of melting point 267°–269° is precipitated by adding ethereal hydrogen chloride solution and is filtered off.

4-(2,3-Dimethyl-6-benzofuranyl)-piperidine hydrochloride of melting point 277° (from methanol/ether) is obtained in an analogous manner using 2.57 g (0.010 mol) of 3-(2,3-dimethyl-6-benzofuranyl)-glutarimide.

The starting materials can be prepared as follows:

(a) 52.6 g (0.404 mol) of ethyl acetoacetate and 3.6 ml of piperidine are added to a solution of 34.8 g (0.2 mol) of 2,3-dimethyl-5-benzofurancarboxaldehyde [c.f. Example (1a) and (b)] in 100 ml of absolute ethanol. The yellowish solution is left to stand at room temperature for 48 hours. A crystalline precipitate thereby gradually forms. This is ground, filtered off with suction, washed with ethanol and dried under a high vacuum. The diethyl 2-(2,3-dimethyl-5-benzofuranyl-4-hydroxy-4-methyl-6-oxo-1,3-cyclohexanedicarboxylate thus obtained as white crystals melts at 156°–158.5°.

Diethyl 2-(2,3-dimethyl-6-benzofuranyl)-4-hydroxy-4-methyl-6-oxo-1,3-cyclohexanedicarboxylate of melting point 183°–185° is obtained in an analogous manner using 34.8 g (0.2 mol) of 2,3-dimethyl-6-benzofurancarboxaldehyde [c.f. Example (3a) and (b)].

(b) 83.2 g (0.2 mol) of the first diethyl ester obtained according to a) are added in portions to a solution of 160 g (4 mols) of sodium hydroxide in 475 ml of water and 200 ml of ethanol at 90°. The yellow suspension formed is warmed to 90° for 30 minutes. The reaction mixture is then cooled to room temperature, diluted to a total volume of about 1.5 liters with water and rendered acid to Congo Red with concentrated hydrochloric acid, whilst cooling with ice-water. The white precipitate which thereby separates out is filtered off with suction, washed with water and dried, whereupon 3-(2,3-dimethyl-5-benzofuranyl)-glutaric acid is obtained as pale sand-coloured crystals of melting point 203°–205° (after recrystallisation from ethanol/water: 205°–206°).

3-(2,3-Dimethyl-6-benzofuranyl)-glutaric acid of melting point 190°–192° is obtained in an analogous manner using 83.2 g (0.2 mol) of the second diethyl ester prepared according to a).

(c) 27.6 g (0.1 mol) of 3-(2,3-dimethyl-5-benzofuranyl)-glutaric acid are refluxed in 120 ml of acetic anhydride for one hour. The excess reagent and the acetic acid formed are then evaporated off in a rotary evaporator. The brownish residue is dissolved in ether, and hexane is added until crystallisation starts. The crystals are filtered off with suction, washed with ether/hexane and dried. The 3-(2,3-dimethyl-5-benzofuranyl)-glutaric anhydride thus obtained as pale sand-coloured crystals melts at 107°–110°, and after recrystallisation from methylene chloride/hexane, at 111°–112°.

3-(2,3-Dimethyl-6-benzofuranyl)-glutaric anhydride of melting point 145°–147° is obtained in an analogous manner using 27.6 g (0.1 mol) of 3-(2,3-dimethyl-6-benzofuranyl)-glutaric acid.

(d) 77 g (4 mols) of ammonium acetate are added to 25.8 g (0.1 mol) of 3-(2,3-dimethyl-5-benzofuranyl)-glutaric anhydride, the components are mixed thoroughly and the mixture is heated to 160° for 5 hours. It is then cooled and poured onto an ice-water mixture and the entire mixture is extracted with ethylene chloride. The organic phase is washed until neutral, dried and evaporated. The resulting sand-coloured powder is crystallised from dioxan/hexane, whereupon 3-(2,3-dimethyl-5-benzofuranyl)-glutarimide of melting point 183°–185° is obtained.

3-(2,3-Dimethyl-6-benzofuranyl)-glutarimide of melting point 252°–254° is obtained in an analogous manner using 25.8 g (0.1 mol) of 3-(2,3-dimethyl-6-benzofuranyl)-glutaric anhydride.

EXAMPLE 5

4-(2,3-Dimethyl-4-benzofuranyl)-piperidine hydrochloride of melting point 340°–342° (from methanol/ether) is obtained analogously to Example 4 using 2.57 g (0.010 mol) of 3-(2,3-dimethyl-4-benzofuranyl)-gluctarimide.

The starting material can be prepared as follows:

(a) 2,3-Dimethyl-4-benzofuranmethanol is obtained, as a crude product which can be further used direct, analogously to Example (1a) by reducing 19.0 g (0.1 mol) of 2,3-dimethyl-4-benzofurancarboxylic acid [prepared in accordance with the method of Y. Kawasawe and M. Takashima, Bull. Chem. Soc. Japan 40, 1224-1231 (1967)].

(b) 2,3-Dimethyl-4-benzofurancarboxaldehyde is prepared analogously to Example (1b) using 158.2 g (0.9 mol) of 2,3-dimethyl-4-benzofuranmethanol.

(c) to (f) The intermediates indicated below are obtained analogously to Example (4a) to (4d) using in each case the same amounts of the corresponding isomeric starting materials, the intermediates being (c) diethyl 2-(2,3-dimethyl-4-benzofuranyl)-4-hydroxy-4-methyl-6-oxo-1,3-cyclohexanedicarboxylate of melting point 179°–180°;

(d) 3-(2,3-dimethyl-4-benzofuranyl)-glutaric acid of melting point 210°–211.5°;

(e) 3-(2,3-dimethyl-4-benzofuranyl)-glutaric anhydride of melting point 138°–139°; and (f) 3-(2,3-dimethyl-4-benzofuranyl)-glutarimide of melting point 214°–215° (from dioxan/ether).

EXAMPLE 6

4-(2,3-Dimethyl-7-benzofuranyl)-piperidine hydrochloride of melting point 287°–288° (from methanol/ether) is obtained analogously to Example 4 using 2.57 g (0.010 mol) of 3(2,3-dimethyl-7-benzofuranyl)-glutarimide.

The starting material can be prepared as follows:

(a) 135 g (0.6 mol) of 1-methyl-2-propynyl) p-toluenesulfonate [H. Schmid et al., Helv. Chim. Acta 55, 1133 (1972)] and 207 g (1.5 mols) of potassium carbonate are added to a solution of 100 g (0.6 mol) of ethyl salicylate in 300 ml of acetone. This reaction mixture is refluxed for 72 hours. The brownish reaction mixture is then cooled and filtered, the material on the filter is washed with acetone and the combined filtrates are evaporated in a rotary evaporator. The resulting brown oil is dissolved in ether and the solution is washed three times with 2 N sodium hydroxide solution and then with saturated sodium chloride solution until neutral. The ethereal solution is dried and evaporated in a rotary evaporator. The residue is fractionated under a high vacuum, whereupon ethyl o-(1-methyl-2-propynyloxy)-benzoate of boiling point 73°–75°/0.005 mm Hg is obtained.

(b) 17 g of mercury-II sulfate are dissolved in 215 ml of water and 55 ml of ethanol, the solution is warmed to 40° and 98.0 g (0.45 mol) of ethyl o-(1-methyl-2-propynyloxy)-benzoate are added dropwise at this temperature in the course of about 20 minutes. When the addition has ended, the reaction mixture is stirred at 45°–50° for one hour. It is then cooled and filtered through diatomaceous earth, in order to separate off the mercury which has separated out, and the material on the filter is washed with ether. The filtrate is dried and evaporated. The red oil which remains is dissolved in 250 ml of methylene chloride, and 5 ml of 30% aqueous hydrogen peroxide solution are added, whereupon a red precipitate of mercury-II oxide separates out immediately. After 30 minutes, the entire mixture is filtered through diatomaceous earth and the filtrate is shaken with water several times, until the potassium iodide test is negative, and is dried and evaporated in a rotary evaporator. The residue is fractionated under a high vacuum, whereupon ethyl o-(1-methyl-2-oxopropoxy)-benzoate of boiling point 86°–87°/0.01 mm Hg is obtained.

(c) 35.4 g (0.15 mol) of the above ethyl ester and 15 ml of absolute ethanol are cooled in an ice-water bath. 34 g (18.5 mols) of concentrated sulfuric acid are then added dropwise in the course of 20 minutes. The temperature thereby rises, and is kept at 10°–15°. Thereafter, the reaction mixture is allowed to warm to room temperature (time: about 15 minutes) and is then heated to an internal temperature of 55° for 60 minutes. Thereafter, the red-brown coloured reaction mixture is cooled and then poured onto a mixture of about 50 g of ice and 100 ml of ethyl acetate. The organic phase is separated off and washed first three times with water, then three times with aqueous 1 N sodium bicarbonate solution and finally with saturated sodium chloride solution and is then dried with sodium sulfate and evaporated in a rotary evaporator. The yellow oil which remains is distilled under a high vacuum, whereupon ethyl 2,3-dimethyl-7-benzofurancarboxylate is obtained as a colourless oil, which becomes pale yellow on standing, of boiling point 93.5°–95°/0.005 mm Hg.

(d) 21.8 g (0.1 mol) of the ester obtained according to c) are dissolved in 50 ml of tetrahydrofuran and the solution is added in portions to a suspension of 3.7 g of lithium aluminium hydride in 150 ml of tetrahydrofuran, with ice-cooling and under a nitrogen atmosphere. When the addition has ended, the cooling bath is removed and the mixture is stirred at room temperature for a further 3 hours. The reaction mixture is again cooled to 0° and 11 ml of water and 7.5 ml of 2 N sodium hydroxide solution are then added slowly. After stirring the mixture for a further 30 minutes, it is filtered over diatomaceous earth. The material on the filter is washed with tetrahydrofuran and the combined filtrates are evaporated in a rotary evaporator. The residue is recrystallised twice from ether/hexane, whereupon 2,3-dimethyl-7-benzofuranmethanol is obtained as white crystals of melting point 65.5°-66.5°.

(e) 17.6 g (0.1 mol) of 2,3-dimethyl-7-benzofuranmethanol are dissolved in 200 ml of toluene, and 18 g of manganese dioxide are added, with stirring. The black suspension is stirred at room temperature for 7 days and each day a further 5 g of manganese dioxide are added. Thereafter, the manganese dioxide is filtered off and the toluene solution is evaporated in a rotary evaporator, whereupon 2,3-dimethyl-7-benzofurancarboxaldehyde is obtained as pale yellowish crystals of melting point 63°-65°.

(f) to (i) The intermediates indicated below are obtained analogously to Example (4a) to (d), using in each case the same amounts of the corresponding isomeric starting materials, the intermediates being (f) diethyl 2-(2,3-dimethyl-7-benzofuranyl)-4-hydroxy-4-methyl-6-oxo-1,3-cyclohexanedicarboxylate of melting point 130°-132°;

(g) 3-(2,3-dimethyl-7-benzofuranyl)-glutaric acid of melting point 193°-195°;

(h) 3-(2,3-dimethyl-7-benzofuranyl)-glutaric anhydride of melting point 143°-144°; and (i) 3-(2,3-dimethyl-7-benzofuranyl)-glutarimide of melting point 209°-211° (from methanol/ether).

EXAMPLE 7

1-Methyl-4-(2,3-dimethyl-6-benzofuranyl)-piperidine is obtained analogously to Example 4 using 2.71 g (0.010 mol) of N-methyl-(2,3-dimethyl-6-benzofuranyl)-glutarimide. The crude base is dissolved in about 10 times the amount (weight/volume) of a 1:4 mixture of methanol/ether and the solution is adjusted to a pH value of about 3 by adding an ethereal solution of maleic acid, whereupon acid 1-methyl-4-(2,3-dimethyl-6-benzofuranyl)-piperidine 1:1 maleate of melting point 149°-150° crystallises out immediately. The starting material is prepared as follows:

(a) 3.87 g (0.015 mol) of 3-(2,3-dimethyl-6-benzofuranyl)-glutaric anhydride [c.f. Example (4a) to (e)] are dissolved in 12.5 ml of toluene and 12.5 ml of glacial acetic acid. 10 ml of a 1.88 molar solution of methylamine in toluene are added to this solution at room temperature and the reaction mixture is heated to the boiling point for 6½ hours, using a water separator. The cooled reaction mixture is poured onto an ice-water mixture and extracted with ether and the organic phase is washed with sodium bicarbonate and saturated sodium chloride solution until neutral. The organic phase is then dried over sodium sulfate and evaporated in a rotary evaporator. N-Methyl-3-(2,3-dimethyl-6-benzofuranyl)-glutarimide thus obtained as sand-coloured crystals of melting point 182°-185° crystallises spontaneously.

EXAMPLE 8

A solution of 2.57 g (0.010 mol) of 1-formyl-4-(2,3-dimethyl-6-benzofuranyl)-piperidine in 15 ml of tetrahydrofuran is added dropwise to a suspension, cooled with an ice-water mixture, of 0.456 g (0.012 mol) of lithium aluminium hydride in 15 ml of absolute ether in the course of 10 minutes, whereupon an exothermic reaction starts. 2.5 ml of 1 N sodium hydroxide solution are added to the reaction mixture, with ice-cooling, and the mixture is stirred in an ice-water bath for a further 30 minutes. The white suspension is filtered off with suction, the residue on the filter is washed with ethyl acetate and the filtrate is evaporated in a rotary evaporator, whereupon crude 1-methyl-4-(2,3-dimethyl-6-benzofuranyl)-piperidine is obtained as a yellowish oil. The acid 1:1 maleate prepared therefrom analogously to Example 7 melts at 149°-150°.

The starting material can be prepared as follows:

(a) 2.29 g (0.10 mol) of 4-(2,3-dimethyl-6-benzofuranyl)-piperidine (c.f. Example 3) are refluxed in 23 ml of ethyl formate for 2 hours. Thereafter, the clear, brownish reaction solution is evaporated in a rotary evaporator, whereupon 1-formyl-4-(2,3-dimethyl-6-benzofuranyl)-piperidine remains as sand-coloured crystals of melting point 86°-90°. A sample recrystallised from ether/hexane melts at 89°-91°, but the product obtained on evaporation is sufficiently pure for subsequent reduction.

EXAMPLE 9

A solution of 28.3 g (0.1 mol) of 3-(6,7,8,9-tetrahydro-2-dibenzofuranyl)-glutarimide in 250 ml of tetrahydrofuran is added dropwise to a suspension of 7.6 g (0.2 mol) of lithium aluminium hydride in 250 ml of tetrahydrofuran at 0° in the course of one hour, with ice-water cooling. The reaction mixture is subsequently stirred at room temperature for a further 3 hours and then cooled again to 0°. At this temperature, first 7.6 ml of water, then 7.6 ml of 2 N sodium hydroxide solution and thereafter 22.8 ml of water are added dropwise. The suspension formed is stirred at room temperature for 30 minutes and then filtered over diatomaceous earth. The filtrate is dried over sodium sulfate and evaporated to dryness under a waterpump vacuum, whereupon crude 4-(6,7,8,9-tetrahydro-2-dibenzofuranyl)-piperidine is obtained as an amorphous yellow foam. The corresponding hydrochloride is obtained in the form of white crystals of melting point 260°-262° by reacting the base in methanol with a solution of hydrogen chloride in ether.

Crude 4-(6,7,8,9-tetrahydro-1-dibenzofuranyl)-piperidine, and from this the corresponding hydrochloride of melting point 291°-293° (from methanol/ether), are obtained in an analogous manner using 28.3 g (0.1 mol) of 3-(6,7,8,9-tetrahydro-1-dibenzofuranyl)-glutarimide.

The starting materials can be prepared as follows:

(a) 166.2 g (1 mol) of ethyl p-hydroxybenzoate and 132.6 g (1 mol) of 2-chlorocyclohexanone are dissolved in 1,500 ml of dry acetone, and 415 g (3 mols) of anhydrous potassium carbonate are added. The mixture is refluxed for 20 hours and then cooled to room temperature. The suspension formed is filtered and the filtrate is evaporated under a waterpump vacuum. The oily residue is dissolved in 500 ml of ethyl acetate and the organic solution is washed twice with 200 ml of cold 1 N sodium hydroxide solution each time and once with 250 ml of ice-water, dried over sodium sulfate and evaporated to dryness under a waterpump vacuum. The resulting yellow oil is distilled under a high vacuum, whereupon ethyl p-(2-oxocyclohexyloxy)-benzoate of boiling point 158°-164° C./0.1 mm Hg is obtained. This ester can be crystallised from ether/hexane and has a melting point of 66°-68°.

Ethyl m-(2-oxocyclohexyloxy)-benzoate of boiling point 140°-160°/0.08 mm Hg and melting point 65°-66° is obtained in an analogous manner using 166.2 g (1 mol) of ethyl m-hydroxybenzoate.

(b) 262.3 g (1 mol) of ethyl p-(2-oxocyclohexyloxy)-benzoate are cooled to 10° and 250 ml of concentrated sulfuric acid are added dropwise in the course of about 2 hours. During this addition, the temperature is kept at between 10° and 20° with an ice-water bath. When the addition has ended, the mixture is stirred at room temperature for a further 3 hours and then poured onto a 2:1 mixture of saturated aqueous sodium carbonate solution and ice. The aqueous phase is extracted once with about 1,000 ml of ether and then a further three times with 300 ml of ether each time and the combined organic phases are washed four times with 300 ml of 2 N sodium hydroxide solution each time, dried over sodium sulfate and evaporated under a waterpump vacuum. The oily residue is purified by filtration over a layer of silica gel, chloroform being used as the solvent and eluting agent. After evaporating off the chloroform, ethyl 6,7,8,9-tetrahydro-2-dibenzofurancarboxylate is obtained as a yellowish oil.

The alkaline aqueous phase which remains after the extraction with ether is rendered acid with concentrated hydrochloric acid. The substance which has precipitated is filtered off, washed thoroughly with water and dried under a high vacuum, whereupon amorphous 6,7,8,9-tetrahydro-2-dibenzofurancarboxylic acid is obtained.

Oily ethyl 6,7,8,9-tetrahydro-1-dibenzofurancarboxylate, together with the free 6,7,8,9-tetrahydro-1-dibenzofurancarboxylic acid of melting point 150°–153°, are obtained analogously starting from 262.3 g (1 mol) of ethyl m-(2-oxocyclohexyloxy)-benzoate.

($c^1$) 122 g (0.5 mol) of ethyl 6,7,8,9-tetrahydro-2-dibenzofurancarboxylate are dissolved in 300 ml of tetrahydrofuran and the solution is added dropwise to a suspension, cooled to 0°, of 20 g (0.52 mol) of lithium aluminium hydride in 300 ml of tetrahydrofuran in the course of about one hour. The mixture is then stirred at 0° for one hour and at room temperature for 3 hours and then cooled again to 0°. At this temperature, first 20 ml of water, then 20 ml of 2 N sodium hydroxide solution and thereafter 60 ml of water are added dropwise. The suspension formed is stirred at room temperature for 30 minutes and then filtered over diatomaceous earth. The residue on the filter is washed with ether and the combined filtrates are dried over sodium sulfate and evaporated under a waterpump vacuum, whereupon 6,7,8,9-tetrahydro-2-dibenzofuranmethanol remains as a yellowish oil. It can be recrystallised from ethyl acetate/toluene and then melts at 63°–65°.

($c^2$) 6,7,8,9-Tetrahydro-2-dibenzofuranmethanol is likewise obtained from 0.5 mol (108 g) of 6,7,8,9-tetrahydro-2-dibenzofurancarboxylic acid by the same process.

6,7,8,9-Tetrahydro-1-dibenzofuranmethanol is obtained as yellowish crystals of melting point 43°–45° in an analogous manner using the same amounts of ethyl 6,7,8,9-tetrahydro-1-dibenzofurancarboxylate or free 6,7,8,9-tetrahydro-1-dibenzofurancarboxylic acid.

(d) 40.4 g (0.2 mol) of 6,7,8,9-tetrahydro-2-dibenzofuranmethanol are dissolved in 800 ml of toluene and 176 g (2 mols) of manganese dioxide are added. The dark suspension is stirred at room temperature for 72 hours and then filtered over diatomaceous earth and the resulting filtrate is evaporated to dryness under a waterpump vacuum. 6,7,8,9-Tetrahydro-2-dibenzofurancarboxaldehyde is thus obtained as a dark yellow oily product which, according to the thin layer chromatogram (toluene/ethyl acetate 1:1) is a single compound and can be used for further reactions without additional purification.

6,7,8,9-Tetrahydro-1-dibenzofurancarboxaldehyde is obtained as yellowish crystals of melting point 55°–57° in an analogous manner starting from 40.4 g (0.2 mol) of 6,7,8,9-tetrahydro-1-dibenzofuranmethanol.

(e) 52.0 g (0.4 mol) of ethyl acetoacetate and 6 ml of pyridine are added to a solution of 40.0 g (0.2 mol) of 6,7,8,9-tetrahydro-2-dibenzofurancarboxaldehyde in 500 ml of absolute ethanol. On stirring the mixture at room temperature, a crystalline precipitate gradually forms. After stirring for 72 hours, this precipitate is filtered off, washed with hexane and dried under a high vacuum, whereupon diethyl 2-(6,7,8,9-tetrahydro-2-dibenzofuranyl)-4-hydroxy-4-methyl-6-oxo-1,3-cyclohexanedicarboxylate is obtained as yellowish crystals of melting point 168°–170°. A sample recrystallised from ethanol melts at 171°–173°.

Diethyl 2-(6,7,8,9-tetrahydro-1-dibenzofuranyl)-4-hydroxy-4-methyl-6-oxo-1,3-cyclohexanedicarboxylate is obtained analogously as light yellow crystals of melting point 155°–157° using 40.0 g (0.2 mol) of 6,7,8,9-tetrahydro-1-dibenzofurancarboxaldehyde.

(f) A solution of 44.2 g (0.1 mol) of diethyl 2-(6,7,8,9-tetrahydro-2-dibenzofuranyl)-4-hydroxy-4-methyl-1,3-cyclohexanedicarboxylate in 250 ml of dioxan is added dropwise to a solution of 120 g (3 mols) of sodium hydroxide in 125 ml of water with 250 ml of ethanol at 90° in the course of 30 minutes. The reaction mixture is heated to 90° for 30 minutes and then concentrated to about ⅓rd of its volume by distilling off the solvents. After diluting the mixture with 750 ml of water, 350 ml of concentrated hydrochloric acid are added, with ice-water cooling. The crude acid which has precipitated is filtered off, washed thoroughly with water and dried. 3-(6,7,8,9-Tetrahydro-2-dibenzofuranyl)-glutaric acid is thus obtained as light yellow-brown crystals of melting point 165°–170°. A sample crystallised from ethanol/water melts at 169°–174°.

3-(6,7,8,9-Tetrahydro-1-dibenzofuranyl)-glutaric acid is obtained analogously as yellowish crystals of melting point 176°–181° using 44.2 g (0.1 mol) of the second diethyl ester obtained according to (e).

(g) 30.2 g (0.1 mol) of 3-(6,7,8,9-tetrahydro-2-dibenzofuranyl)-glutaric acid are refluxed with 100 ml of acetic anhydride for 1½ hours. On leaving the cooled dark solution to stand, a crystalline precipitate forms and is filtered off after 48 hours and washed with cold toluene. The 3-(6,7,8,9-tetrahydro-2-dibenzofuranyl)-glutaric anhydride thus obtained melts at 164°–166°. After concentrating the filtrate under a waterpump vacuum, an addititonal amount of 3-(6,7,8,9-tetrahydro-2-dibenzofuranyl)-glutaric anhydride is obtained as yellowish crystals with the same melting point.

3-(6,7,8,9-Tetrahydro-1-dibenzofuranyl)-glutaric anhydride is obtained as yellow crystals of melting point 139°–140° in an analogous manner using 30.2 g (0.1 mol) of 3-(6,7,8,9-tetrahydro-1-dibenzofuranyl)-glutaric acid.

($h^1$) 28.4 g (0.1 mol) of 3-(6,7,8,9-tetrahydro-2-dibenzofuranyl-2-glutaric anhydride are added in portions to 100 ml of 25% aqueous ammonia solution at 40°. The mixture is heated to 70° for one hour and then evaporated to dryness under a waterpump vacuum. The yellow residue is then heated to 150° for 3 hours. The resulting grey-brown product is dissolved in 300 ml of dioxan and crystallisation is effected by adding ether, whereupon 3-(6,7,8,9-tetrahydro-2-dibenzofuranyl)-glutarimide is obtained as light yellow-brown crystals of melting point 184°–193°.

The above imide can also be prepared equally as well analogously to (h²).

(h²) 28.4 g (0.1 mol) of 3-(6,7,8,9-tetrahydro-1-dibenzofuranyl)-glutaric anhydride are heated to 150° together with 77 g (1 mol) of ammonium acetate. After 2 and 6 hours, in each case 20 g of ammonium acetate are again added to the clear, dark melt. After 8 hours, the melt is poured onto 1 liter of an ice-water mixture. The 3-(6,7,8,9-tetrahydro-1-dibenzofuranyl)-glutarimide which has thereby precipitated is filtered off, dried and recrystallised from dioxan/ether, whereupon it is obtained as grey crystals of melting point 229°–231°.

The above imide can also be prepared analogously to (h¹).

EXAMPLE 10

15.0 g (0.06 mol) of 1-methyl-4-(2-methyl-5-benzofuranyl)-4-piperidinol are dissolved in 250 ml of hexamethylphosphoric acid triamide and the solution is heated to 230° for one hour under an inert atmosphere of nitrogen. After cooling, the solvent is distilled off at 110° under a waterpump vacuum, the dark brown, oily residue is dissolved in toluene and the organic phase is extracted with an approximately 10% aqueous solution of methanesulfonic acid. The acid extract is washed twice with toluene, then adjusted to pH 10 in the cold with concentrated sodium hydroxide solution and extracted with chloroform. The organic phase is washed with water, dried over sodium sulfate and evaporated to dryness under a waterpump vacuum. The oily residue is distilled under a high vacuum, whereupon 1-methyl-4-(2-methyl-5-benzofuranyl)-1,2,3,6-tetrahydro-pyridine or boiling point 115°–128°/0.03 mm Hg and melting point 59°–62° is obtained. The hydrochloride, prepared with hydrogen chloride in ethyl acetate, melts at 195°–197°.

The starting material is prepared as follows:

(a) 63.3 g (0.3 mol) of 2-methyl-5-bromo-benzofuran are dissolved in 200 ml of dry ether, the solution is cooled to −10° in an ice-sodium chloride bath and 200 ml of an approximately 2 molar solution of butyl-lithium in hexane are added dropwise. During this addition, the temperature is not allowed to rise above 0°. The reaction mixture is kept at this temperature for one hour, and a solution of 34 g (0.3 mol) of 1-methyl-4-piperidinone in 100 ml of dry ether is then added dropwise. The internal temperature is kept between 0° and +10°. The reaction mixture is subsequently stirred at room temperature for 15 hours and then poured onto about 300 ml of an ice-water mixture. The organic phase is separated off and the aqueous phase is extracted twice with 100 ml of ethyl acetate each time. The organic phases are combined, washed with water and then extracted twice with an approximately 10% aqueous solution of methanesulfonic acid. The combined acid solutions are filtered over diatomaceous earth and the filtrate is cooled with an ice-water mixture, rendered alkaline with concentrated sodium hydroxide solution and extracted three times with chloroform. The organic phases are combined, dried over sodium sulfate and evaporated to dryness under a waterpump vacuum. The resulting crude product is crystallised from 2,000 ml of hexane, whereupon 1-methyl-4-(2-methyl-5-benzofuranyl)-4-piperidinol of melting point 118°–120° is obtained. The hydrochloride, prepared from the free base with hydrogen chloride, crystallises from acetone and has a melting point of 188°–191°.

EXAMPLE 11

10.8 g of 1-methyl-4-(2-methyl-5-benzofuranyl)-1,2,3,6-tetrahydropyridine (c.f. Example 10) are hydrogenated in 100 ml of methanol in the presence of 1.0 g of a palladium-on-charcoal catalyst (5% of Pd) at room temperature and under normal pressure until the equimolar amount of hydrogen has been taken up. The catalyst is then filtered off, the methanol is evaporated off and the residue is distilled under a high vacuum, whereupon 1-methyl-4-(2-methyl-5-benzofuranyl)-piperidine is obtained as an oil of boiling point 112°–124°/0.01 mm Hg. The hydrochloride, prepared in the customary manner in ethyl acetate, melts between 220° and 235°.

EXAMPLE 12

7.3 g (0.03 mol) of 1-methyl-4-(2-methyl-5-benzofuranyl)-piperidine (c.f. Example 11) are stirred, together with 11.0 g (0.1 mol) of ethyl chloroformate, in 125 ml of toluene at 50°–55° for 15 hours. The solvent and excess ethyl chloroformate are distilled off under a waterpump vacuum at a bath temperature of 70°, the resulting residue is dissolved in toluene and the toluene solution is washed with water, 2 N sodium hydroxide solution, water, 2 N hydrochloric acid and water again. The toluene solution is then dried over sodium sulfate and evaporated to dryness under a waterpump vacuum. Crude ethyl 4-(2-methyl-2-benzofuranyl)-1-piperidinecarboxylate which remains as an oil can be further used directly. 9.1 g (0.03 mol) of the above crude ester and 15 g of solid potassium hydroxide are dissolved in 55 ml of diethylene glycol and 10 ml of water and the solution is refluxed for 15 hours in a nitrogen atmosphere. After cooling, the reaction mixture is diluted with 250 ml of toluene and the organic phase is separated off, washed with water and then extracted with 10% aqueous methanesulfonic acid solution. The acid extract is washed with toluene, rendered strongly alkaline in the cold with concentrated sodium hydroxide solution and extracted with chloroform. The chloroform solution is washed with water, dried over sodium sulfate and evaporated under a waterpump vacuum. The resulting oil is distilled under a high vacuum and gives 4-(2-methyl-5-benzofuranyl)-piperidine of boiling point 108°–111°/0.015 mm Hg.

The hydrochloride of melting point 212°–124° is obtained therefrom in the customary manner.

EXAMPLE 13

2.8 g (0.013 mol) of 4-(2-methyl-5-benzofuranyl)-piperidine (c.f. Example 12) and 2.4 g (0.02 mol) of 2-propynyl bromide are dissolved in a suspension of 10 g of potassium carbonate in 120 ml of methanol and the solution is stirred at room temperature. After 24 hours, a further 0.24 g of 2-propynyl bromide is added and the reaction mixture is stirred at room temperature for a further 24 hours. Thereafter, it is filtered, the residue on the filter is washed with ethyl acetate and the combined filtrates are evaporated to dryness under a waterpump vacuum. The residue is dissolved again in ethyl acetate and the solution is washed three times with water, dried over sodium sulfate and evaporated to dryness under a waterpump vacuum. The resulting residue is chromatographed on 200 g of aluminium oxide (eluting agent: methylene chloride), whereupon, after evaporating off the solvent, crystalline 1-(2-propynyl)-4-(2-methyl-5-benzofuranyl)-piperidine is obtained. The hydrochloride, prepared from the base in a conventional manner, melts at 185°–187°.

EXAMPLE 14

4.15 g (0.030 mol) of anhydrous potassium carbonate are added to a solution of 2.29 g (0.010 mol) of 4-(2,3-dimethyl-5-benzofuranyl)-piperidine (c.f. Example 1) in 25 ml of acetone, and a solution of 1.3 g (0.011 mol) of 2-propynyl bromide in 11 ml of acetone is added dropwise in the course of 10 minutes, with stirring. The reaction mixture is heated to 40° for 4 hours and then cooled to room temperature and the inorganic salts are filtered off. The filtrate is evaporated in a rotary evaporator. The brown oil which remains has, in the thin layer chromatogram (silica gel/5% methanol/chloroform), a main spot at an Rf value of about 0.7, in addition to 4 secondary spots. The resulting oil is chromatographed on 50 g of silica gel using chloroform as the solvent and eluting agent, whereupon 1-(2-propynyl)-4-(2,3-dimethyl-5-benzofuranyl)-piperidine is obtained, as the main fraction, as a yellowish oil with an Rf value of about 0.7. This base is dissolved in about 3 ml of methanol and converted into the hydrochloride by acidifcation with hydrogen chloride solution and the hydrochloride is made to crystallise by adding about 20 ml of ether and is filtered off with suction. The hydrochloride thus obtained as white crystals melts at 224°–225°.

EXAMPLE 15

Analogously to Example 8, by reduction by means of lithium aluminium hydride,
1-methyl-4-(2,3-dimethyl-4-benzofuranyl)-piperidine and its 1:1-maleate are obtained from 2.57 g (0.010 mol) of
1-formyl-4-(2,3-dimethyl-4-benzofuranyl)-piperidine,
1-methyl-4-(2,3-dimethyl-7-benzofuranyl)-piperidine and its 1:1-maleate are obtained from 2.57 g (0.010 mol) of
1-formyl-4-(2,3-dimethyl-7-benzofuranyl)-piperidine,
1-methyl-4-(6,7,8,9-tetrahydro-2-dibenzofuranyl)-piperidine and its 1:1-maleate are obtained from 2.83 g (0.010 mol) of 1-formyl-4-(6,7,8,9-tetrahydro-2-dibenzofuranyl)-piperidine, and
1-methyl-4-(6,7,8,9-tetrahydro-1-dibenzofuranyl)-piperidine and its 1:1-maleate are obtained from 2.83 g (0.010 mol) of 1-formyl-4-(6,7,8,9-tetrahydro-1-dibenzofuranyl)-piperidine.

The hydrochlorides of the above bases can also be prepared, for example, in a conventional manner in place of the 1:1-maleates.

The 1-formyl compounds required as starting materials are prepared analogously to Example (8a) from the corresponding compounds, without the 1-substituent, described in Examples 5, 6 and 9.

EXAMPLE 16

Analogously to Example 14,
1-(2-propynyl)-(2,3-dimethyl-6-benzofuranyl)-piperidine and its hydrochloride are obtained using 2.29 g (0.010 mol) of 4-(2,3-dimethyl-6-benzofuranyl)-piperidine (c.f. Example 3),
1-(2-propynyl)-2,3-dimethyl-4-benzofuranyl)-piperidine and its hydrochloride are obtained using 2.29 g (0.010 mol) of 4-(2,3-dimethyl-4-benzofuranyl)-piperidine (c.f. Example 5),
1-(2-propynyl)-4-(2,3-dimethyl-7-benzofuranyl)-piperidine and its hydrochloride are obtained using 2.29 g (0.010 mol) of 4-(2,3-dimethyl-7-benzofuranyl)-piperidine (c.f. Example 6),
1-(2-propynyl)-4-(6,7,8,9-tetrahydro-2-dibenzofuranyl)-piperidine and its hydrochloride are obtained using 2.55 g (0.010 mol) of 4-(6,7,8,9-tetrahydro-2-dibenzofuranyl)-piperidine (c.f. Example 9), and
1-(2-propynyl)-4-(6,7,8,9-tetrahydro-1-dibenzofuranyl)-piperidine and its hydrochloride are obtained using 2.55 g (0.010 mol) of 4-(6,7,8,9-tetrahydro-1-dibenzofuranyl)-piperidine (c.f. Example 9).

EXAMPLE 17

Analogously to Example 4, 14.4 g (0.050 mol) of 3-(2,3-dimethyl-7-methoxy-5-benzofuranyl)-glutarimide are reduced in a suspension of 3.8 g (0.10 mol) of lithium aluminium hydride in 500 ml of ether and the resulting base of melting point 75°–77° is converted into 4-(2,3-dimethyl-7-methoxy-5-benzofuranyl)-piperidine hydrochloride of melting point 277°–277.5°.

The starting material is prepared as follows:

(a) 196.2 g (1.0 mol) of ethyl 4-hydroxy-3-methoxybenzoate (ethyl vanillate) and 106.5 g (1.0 mol) of 3-chloro-2-butanone are dissolved in 1,100 ml of dry acetone, and 415 g (3.0 mols) of anhydrous potassium carbonate are added. The mixture is refluxed for 24 hours and then cooled to room temperature. The suspension formed is filtered and the filtrate is concentrated under a waterpump vacuum. The oily residue is distilled directly under a high vacuum, whereupon ethyl 3-methoxy-4-(1-methyl-2-oxopropoxy)-benzoate of boiling point 132°–134° (0.1 mm Hg) is obtained as a viscous, pale yellowish oil.

(b) 1,600 ml of 70% sulfuric acid are added to 214 g (0.8 mol) of ethyl 3-methoxy-4-(1-methyl-2-oxopropoxy)-benzoate at room temperature. During this addition, the reaction mixture becomes dark-red to brown in colour. Thereafter, the reaction mixture is warmed to 60° for 4 hours. A brown crystalline sludge thereby gradually forms. The reaction mixture is allowed to cool to room temperature and is poured onto 2 kg of ice and extracted with ethyl acetate. The extract is washed twice with water and then 5 times with 500 ml of 0.5 N sodium bicarbonate solution each time and 3 times with 500 ml of 2 N sodium carbonate solution each time, dried over magnesium sulfate and evaporated completely under a waterpump vacuum. Chromatography on 1.5 kg of silica gel using chloroform which contains 2% of methanol gives ethyl 2,3-dimethyl-7-methoxy-5-benzofurancarboxylate, which, after recrystallisation from warm hexane, melts at 67°–68°.

The sodium carbonate extracts obtained above are combined, rendered acid (pH about 2–3) with 5 N hydrochloric acid and then extracted with ethyl acetate.

The new ethyl acetate phase thus obtained is likewise dried over magnesium sulfate and then evaporated under a waterpump vacuum. Recrystallisation of the residue from ethyl acetate gives 2,3-dimethyl-7-methoxy-5-benzofurancarboxylic acid of melting point 229°–231°.

Analogous working up of the sodium bicarbonate extracts gives, in addition to the acid described above, mainly the acid formed by saponification of the ester group of the starting material, in addition to a little vanillic acid.

(c) 49.6 g (0.2 mol) of ethyl 2,3-dimethyl-7-methoxy-5-benzofurancarboxylate [or 44.1 g (0.20 mol) of the corresponding free acid] are reduced in a suspension of 7.8 g (0.2 mol) of lithium aluminium hydride in 300 ml of anhydrous tetrahydrofuran analogously to Example (1a) to give 2,3-dimethyl-7-methoxy-5-benzofuranmethanol of melting point 83°–84°.

(d) 61.8 g (0.3 mol) of 2,3-dimethyl-7-methoxy-5-benzofuranmethanol are oxidised with 135 g of manganese dioxide in 500 ml of toluene analogously to Example (1b) to give 2,3-dimethyl-7-methoxy-5-benzofurancarboxaldehyde of melting point 80°–81°.

(e) 61.2 g (0.3 mol) of 2,3-dimethyl-7-methoxy-5-benzofurancarboxaldehyde are subjected to a condensation reaction with 78.9 g (0.606 mol) of ethyl acetoacetate in the presence of 5.4 ml of piperidine in 150 ml of ethanol analogously to Example (4a) to give diethyl 2-(2,3-dimethyl-7-methoxy-5-benzofuranyl)-4-hydroxy-4-methyl-6-oxo-1,3-cyclohexanedicarboxylate of melting point 157°–158°.

(f) 67 g (0.15 mol) of the reaction product from (e) are converted into 3-(2,3-dimethyl-7-methoxy-2-benzofuranyl)-glutaric acid of melting point 168°–169° analogously to Example (4b) by warming with 120 g (3 mols) of sodium hydroxide in 360 ml of water and 150 ml of ethanol.

(g) 3-(2,3-Dimethyl-7-methoxy-5-benzofuranyl)-glutaric anhydride of melting point 194°–195° is obtained analogously to Example (4c) by boiling 45.9 (0.15 mol) of the dicarboxylic acid obtained according to (f) in 180 ml of acetic anhydride.

(h) 3-(2,3-Dimethyl-7-methoxy-5-benzofuranyl)-glutarimide of melting point 220°–222° is obtained analogously to Example (4d) by reacting 28.8 g (0.1 mol) of the anhydride obtained according to (d) with 77 g (4 mols) of ammonium acetate.

EXAMPLE 18

4-(4-Methoxy-6,7,8,9-tetrahydro-2-dibenzofuranyl)-piperidine and its hydrochloride are obtained analogously to Example 9 by reducing 31.3 g (0.1 mol) of 3-(4-methoxy-6,7,8,9-tetrahydro-2-dibenzofuranyl)-glutarimide.

The starting material is prepared as follows:

(a) Ethyl 3-methoxy-4-(2-oxocyclohexyloxy)-benzoate is obtained analogously to Example (9a) using 196.2 g (1 mol) of ethyl 4-hydroxy-3-methoxybenzoate.

(b) Ethyl 4-methoxy-6,7,8,9-tetrahydro-2-dibenzofurancarboxylate is obtained analogously to Example (9b) starting from 292.3 g (1 mol) of ethyl 3-methoxy-4-(2-oxo-cyclohexyloxy)-benzoate.

(c) 4-Methoxy-6,7,8,9-tetrahydro-2-dibenzofuranmethanol is obtained analogously to Example (9c$^1$) by reducing 137 g (0.5 mol) of ethyl 4-methoxy-6,7,8,9-tetrahydro-2-dibenzofurancarboxylate.

(d) 4-Methoxy-6,7,8,9-tetrahydro-2-dibenzofurancarboxaldehyde is obtained analogously to Example (9d) by oxidising 46.4 g (0.2 mol) of 4-methoxy-6,7,8,9-tetrahydro-2-dibenzofuranmethanol.

(e) Diethyl 2-(4-methoxy-6,7,8,9-tetrahydro-2-dibenzofuranyl)-4-hydroxy-4-methyl-6-oxo-1,3-cyclohexanedicarboxylate is obtained analogously to Example (9e) using 46.0 g of the aldehyde obtained according to (d).

(f) 3-(4-Methoxy-6,7,8,9-tetrahydro-2-dibenzofuranyl)-glutaric acid is obtained analogously to Example (9f) starting from 47.2 g (0.1 mol) of the reaction product from (e).

(g) 3-(4-Methoxy-6,7,8,9-tetrahydro-2-dibenzofuranyl)-glutaric anhydride is obtained analogously to Example (9g) starting from 33.2 g (0.1 mol) of 3-(4-methoxy-6,7,8,9-tetrahydro-2-dibenzofuranyl)-glutaric acid.

(h) 3-(4-Methoxy-6,7,8,9-tetrahydro-2-dibenzofuranyl)-glutarimide is obtained analogously to Example (9h$^2$) using 31.4 g (0.1 mol) of the anhydride obtained according to (g).

EXAMPLE 19

2.97 g (0.010 mol) of N-cyclopropyl-3-(2,3-dimethyl-6-benzofuranyl)-glutarimide are reduced analogously to Example 4. 1-Cyclopropyl-4-(2,3-dimethyl-6-benzofuranyl)-piperidine is thereby obtained as a colourless oil. In the thin layer chromatogram on silica gel using, as the running agent, chloroform and 10% methanol, the product has a main spot at an Rf value of 0.6, in addition to a small spot at the start and 2 further secondary spots with Rf values of about 0.3 and 0.8.

(a) 2.58 g (0.01 mol) of 3-(2,3-dimethyl-6-benzofuranyl)-glutaric anhydride (c.f. Example (4c), 0.855 g, corresponding to about 1.04 ml (1.5 molar equivalents) of cyclopropylamine and 11 ml of glacial acetic acid are dissolved in 11 ml of toluene and the solution is refluxed for 2 days using a water separator. The reaction mixture is then cooled to room temperature, diluted with 50 ml of ethyl acetate and washed twice with 25 ml of water. Thereafter, the organic phase is extracted with 2 N aqueous sodium carbonate solution to remove the acid constituents, then washed again with water and with saturated sodium chloride solution (25 ml of each) and dried over sodium sulfate and the ethyl acetate is evaporated off under a waterpump vacuum. A sand-coloured crude product of melting point 180°–182° is thereby obtained. This is recrystallised from warm methylene chloride and hexane, whereupon N-cyclopropyl-3-(2,3-dimethyl-6-benzofuranyl)-glutarimide is obtained as white flakes of melting point 183°–184°.

EXAMPLE 20

7.4 g (0.02 mol) of 1-benzyl-4-(2,3,7-trimethyl-5-benzofuranyl)-piperidine hydrochloride are dissolved in 150 ml of ethanol and, after adding 0.75 g of palladium-on-charcoal (5% of Pd), are hydrogenated for 9 hours under normal pressure and at room temperature. Thereafter, the catalyst is filtered off over diatomaceous earth and the filtrate is evaporated under a waterpump vacuum. The crude product is crystallised from ethanol/ether and 4-(2,3,7-trimethyl-5-benzofuranyl)-piperidine hydrochloride of melting point 307°–308° is obtained.

The starting material is prepared as follows:

(a) Ethyl 4-(1-methyl-2-oxopropoxy)-3-methylbenzoate of boiling point 112°–113° (0.02 mm Hg) is obtained analogously to Example (17a) using 180.2 g (1.0 mol) of ethyl 4-hydroxy-3-methylbenzoate.

(b) 250.3 g (1.0 mol) of ethyl 4-(1-methyl-2-oxopropoxy)-3-methylbenzoate are stirred in 400 ml of 94% sulfuric acid, first at room temperature for 30 minutes and then at 60° for 30 minutes. The reaction mixture is cooled to room temperature, poured onto 2 kg of ice and extracted with ethyl acetate. The organic phase is washed twice with water and then extracted 3 times with 500 ml of 2 N sodium carbonate solution each time. The sodium carbonate solutions are rendered acid (pH about 2–3) with 5 N hydrochloric acid and then extracted with ethyl acetate. The organic phase is dried over magnesium sulfate and evaporated completely under a waterpump vacuum. 2,3,7-Trimethyl-5-benzofurancarboxylic acid of melting point 235°–237° is obtained from the residue by recrystallising it once from hot ethanol.

(c) 46.4 g (0.2 mol) of ethyl 2,3,7-trimethyl-5-benzofurancarboxylate [or 40.8 g (0.2 mol) of the corresponding free acid] are reduced in a suspension of 7.8 g (0.2 mol) of lithium aluminium hydride in 300 ml of anhydrous tetrahydrofuran analogously to Example (1a) to give 2,3,7-trimethyl-5-benzofuranmethanol of melting point 85°–86°.

(d) 57.0 g (0.3 mol) of 2,3,7-trimethyl-5-benzofuranmethanol are oxidised with 135 g of manganese dioxide in 500 ml of toluene analogously to Example (1b) to give 2,3,7-trimethyl-5-benzofurancarboxaldehyde of melting point 57°–58°.

(e) 56.4 g (0.3 mol) of 2,3,7-trimethyl-5-benzofurancarboxaldehyde are subjected to a condensation reaction with 78.9 g (0.606 mol) of ethyl acetoacetate in the presence of 5.4 ml of piperidine in 150 ml of ethanol analogously to Example (4a) to give diethyl 2-(2,3,7-trimethyl-5-benzofuranyl)-4-hydroxy-4-methyl-6-oxo-1,3-cyclohexanedicarboxylate of melting point 168.5°–171°.

(f) 64.6 g (0.15 mol) of the reaction product from (e) are converted into 3-(2,3,7-trimethyl-2-benzofuranyl)-glutaric acid of melting point 167°–169° analogously to Example (4b) by warming with 120 g (3 mols) of sodium hydroxide in 360 ml of water and 150 ml of ethanol.

(g) 3-(2,3,7-Trimethyl-5-benzofuranyl)-glutaric anhydride of melting point 170° is obtained analogously to Example (4c) by boiling 43.5 g (0.15 mol) of the dicarboxylic acid obtained according to (f) in 180 ml of acetic anhydride.

(h) 6-Benzyl-3-(2,3,7-trimethyl-5-benzofuranyl)-glutarimide of melting point 138°–138.5° is obtained analogously to Example 7a using 13.6 g (0.05 mol) of 3-(2,3,7-trimethyl-5-benzofuranyl)-glutaric anhydride and 5.8 g (0.055 mol) of benzylamine in 50 ml of toluene and 50 ml of glacial acetic acid.

(i) 1-Benzyl-4-(2,3,7-trimethyl-5-benzofuranyl)-piperidine hydrochloride of melting point 284°–286° is obtained analogously to Example 4 using 36.1 g (0.1 mol) of 6-benzyl-3-(2,3,7-trimethyl-5-benzofuranyl)-glutarimide and 7.6 g (0.9 mol) of lithium aluminium hydride in 500 ml of ether.

EXAMPLE 21

24.2 g (0.05 mol) of 3-(2,3-dimethyl-7-bromobenzofuranyl)-1,5-pentanediyl dimethanesulfonate are dissolved in 700 ml of 4.4 N ethanolic ammonia solution and the solution is warmed to 65°–70° in a pressure vessel for 16 hours. Thereafter, the reaction mixture is allowed to cool and excess ammonia and the ethanol are removed under a waterpump vacuum. The yellow, oily residue obtained is taken up in ethyl acetate and the resulting solution is extracted with 2 N hydrochloric acid. The acid aqueous solution is filtered through diatomaceous earth and, after cooling with an ice-water mixture, the filtrate is rendered alkaline with 5 N sodium hydroxide solution. The alkaline solution is extracted with ethyl acetate. The ethyl acetate extracts are dried over anhydrous sodium sulfate and evaporated under a waterpump vacuum. The resulting crude base is dissolved in methanol and converted into the hydrochloride with ethereal hydrogen chloride solution. The crude hydrochloride is precipitated by adding ether and is crystallised from ethanol/ether, whereupon 4-(2,3-dimethyl-7-bromo-5-benzofuranyl)-piperidine hydrochloride of melting point 304°–305° is obtained.

The starting material is prepared as follows:

(a) Ethyl 3-bromo-4-(1-methyl-2-oxopropoxy)-benzoate of boiling point 142°–143° (0.11 mm Hg) is obtained analogously to Example 17a) using 244.36 g (1.0 mol) of ethyl 3-bromo-4-hydroxybenzoate.

(b) Analogously to Example (17b), using 315.2 g (1 mol) of ethyl 3-bromo-4-(1-methyl-2-oxopropoxy)-benzoate and 400 g of 94% sulfuric acid, first with ice-cooling, then at room temperature for one hour and thereafter at 50° for 8 hours, ethyl 2,3-dimethyl-7-bromo-5-benzofurancarboxylate of melting point 110°–111° is obtained by recrystallising the neutral portion from hot ethanol, and 2,3-dimethyl-7-bromo-5-benzofuranylcarboxylic acid of melting point 249°–251° is obtained by recrystallising the acid portion from hot ethanol.

(c) 59.4 g (0.2 mol) of ethyl 2,3-dimethyl-7-bromo-5-benzofurancarboxylate [or 53.8 g (0.2 mol) of the corresponding free acid] are reduced in a suspension of 7.8 g (0.2 mol) of lithium aluminium hydride in 300 ml of anhydrous tetrahydrofuran analogously to Example (1a) to give 2,3-dimethyl-7-bromo-5-benzofuranmethanol of melting point 131°–132°.

(d) 76.5 g (0.3 mol) of 2,3-dimethyl-7-bromo-5-benzofuranmethanol are oxidised with 135 g of manganese dioxide in 650 ml of toluene analogously to Example (1b) to give 2,3-dimethyl-7-bromo-5-benzofurancarboxaldehyde of melting point 126°.

(e) 75.9 g (0.3 mol) of 2,3-dimethyl-7-bromo-5-benzofurancarboxaldehyde are subjected to a condensation reaction with 78.9 g (0.606 mol) of ethyl acetoacetate in the presence of 5.4 ml of piperidine in 200 ml of ethanol analogously to Example (4a) to give diethyl 2-(2,3-dimethyl-7-bromo-5-benzofuranyl)-4-hydroxy-4-methyl-6-oxo-1,3-cyclohexanedicarboxylate of melting point 194°–195°.

(f) 74.25 g (0.15 mol) of the reaction product from (c) are converted into 3-(2,3-dimethyl-7-bromo-2-benzofuranyl)-glutaric acid of melting point 197°–198° analogously to Example (4b) by warming with 120 g (3 mols) of sodium hydroxide in 360 ml of water and 150 ml of ethanol.

(g) 53.2 g (0.15 mol) of 3-(2,3-dimethyl-7-bromo-5-benzofuranyl)-glutaric acid are dissolved in 500 ml of anhydrous tetrahydrofuran, and 450 ml (0.45 mol) of a 1.0 molar borane solution in tetrahydrofuran is added, whilst cooling to 5°–10° and with stirring. When the addition of the borane solution has ended, the reaction mixture is allowed to warm to room temperature and is stirred at this temperature for a further 3 hours. Thereafter, the reaction mixture is cooled in an ice-water bath and 225 ml of a 6 N solution of hydrochloric acid in methanol is added dropwise, whereupon hydrogen is set free (in the case of incomplete methanolysis of the boric acid ester formed as an intermediate, this separates out of the milky oil obtained and has a melting point of 143°–146°. Note that hydrogen escapes). The reaction mixture is allowed to warm again to room temperature and is then stirred for a further hour. Thereafter, the solvents are evaporated off under a waterpump vacuum. The milky oil obtained is chromatographed on silica gel using methylene chloride containing 10% of methanol to separate off non-polar by-products. 3-(2,3-Dimethyl-7-bromo-5-benzofuranyl)-1,5-pentanediol of melting point 98°–101° is eluted as the main fraction. After recrystallising once, the pure diol of melting point 102°–103° is obtained.

(h) 16.4 g (0.05 mol) of 3-(2,3-dimethyl-7-bromo-5-benzofuranyl)-1,5-pentanediol are dissolved in 200 ml of pyridine. The solution is cooled to −8° to −10° and 8.5 ml (=12.6 g, 0.11 mol) of methanesulfonyl chloride are added dropwise at this temperature in the course of 30 minutes. The reaction mixture is allowed to react at −8° to −10° for 1½ hours and is then poured onto 500 g of ice and the pH value is adjusted to about 1 by adding 5 N hydrochloric acid. This acid mixture is extracted 3 times with methylene chloride and the extracts are washed twice with 2 N hydrochloric acid and 3 times with water. The combined extracts are dried over sodium sulfate and the solvent is evaporated off under a waterpump vacuum. A crude product which crystallises spontaneously and has a melting point of 154°–156° is thereby obtained. Recrystallisation from methylene chloride/hexane gives 3-(2,3-dimethyl-7-bromo-5-benzofuranyl)-1,5-pentanediyl dimethanesulfonate as white crystals of melting point 158°–159°.

EXAMPLE 22

3.81 g (0.01 mol) of 1-benzyl-4-(2,3-dimethyl-7-cyano-5-benzofuranyl)-piperidine hydrochloride are dissolved in 100 ml of dioxan (anhydrous) and are hydrogenated in the presence of 0.38 g of a 5% palladium-on-charcoal catalyst at room temperature under normal pressure for 11 hours analogously to Example 20. The catalyst is then filtered off over diatomaceous earth and the filtrate is evaporated under a waterpump vacuum. The resulting crude product is recrystallised twice from methanol/ether and 4-(2,3-dimethyl-7-cyano-5-benzofuranyl)-piperidine hydrochloride of melting point 182°–184° is thus obtained.

The starting material is prepared as follows: (a) 3.08 g (0.01 mol) of 4-(2,3-dimethyl-7-bromo-5-benzofuranyl)-piperidine (c.f. Example 21) are dissolved in 100 ml of tetrahydrofuran, and 1.4 ml of triethylamine and then 1.30 ml (0.0105 mol) of benzyl bromide are added to the solution. A white precipitate thereby forms. The reaction mixture is stirred at room temperature for 3½ hours. The solvent and excess triethylamine are then removed under a waterpump vacuum and the residue is added to water. The mixture is extracted 3 times with ether and the combined ether solutions are washed once with 2 N sodium hydroxide solution and then twice with water and once with saturated sodium chloride solution. The combined ether solutions are then dried over sodium sulfate and evaporated completely under a waterpump vacuum. 1-Benzyl-4-(2,3-dimethyl-7-bromo-5-benzofuranyl)-piperidine which melts at 86°–91°, is thereby obtained. In the thin layer chromatogram on silica gel using chloroform/5% methanol as the running agent, this product has an Rf value of 0.4. A sample recrystallised from ether/hexane has a melting point of 88°–91°. The product is of sufficient purity for further use.

(b) 3.98 g (0.01 mol) of 1-benzyl-4-(2,3-dimethyl-7-bromo-5-benzofuranyl)-piperidine and 0.95 g (0.011 mol) of copper-I cyanide are suspended in 22.8 ml of 1-methyl-2-pyrrolidinone and the suspension is heated to 200° for 5½ hours under nitrogen. The black reaction mixture is cooled and poured onto a mixture of 140 ml of 50% aqueous ethylenediamine solution and about 100 g of ice. A deep blue aqueous solution thereby forms. This solution is extracted 3 times with methylene chloride and the organic phases are washed twice with 50% aqueous ethylenediamine solution and then 4 times with water and once with saturated sodium chloride solution. The combined organic extracts are dried over sodium sulfate and, after adding about 50 ml of toluene, evaporated under a waterpump vacuum. A brown-black oil is thereby obtained and is chromatographed on 30 times the amount of silica gel using chloroform as the solvent and eluting agent. The crude base thereby obtained is converted into the hydrochloride in methanol using ethereal hydrogen chloride solution and the hydrochloride is made to crystallise with ether. The crude hydrochloride is recrystallised from methanol/ether and pure 1-benzyl-4-(2,3-dimethyl-7-cyano-5-benzofuranyl)-piperidine hydrochloride of melting point 186°–190° is thus obtained.

EXAMPLE 23

Analogously to Example 8, by reduction by means of lithium aluminium hydride, 1-methyl-4-(2,3-dimethyl-7-methoxy-5-benzofuranyl)-piperidine and its hydrochloride are obtained from 2.87 g (0.01 mol) of 1-formyl-4-(2,3-dimethyl-7-methoxy-5-benzofuranyl)-piperidine, 1-methyl-4-(2,3,7-trimethyl-5-benzofuranyl)-piperidine and its hydrochloride are obtained from 2.71 g (0.01 mol) of 1-formyl-4-(2,3,7-trimethyl-5-benzofuranyl)-piperidine, 1-methyl-4-(4-methoxy-6,7,8,9-tetrahydro-2-dibenzofuranyl)-piperidine and its hydrochloride are obtained from 3.13 g (0.01 mol) of 1-formyl-4-(4-methoxy-6,7,8,9-tetrahydro-2-dibenzofuranyl)-piperidine and 1-methyl-4-(4-methyl-6,7,8,9-tetrahydro-2-dibenzofuranyl)-piperidine and its hydrochloride are obtained from 2.97 g (0.01 mol) of 1-formyl-4-(4-methyl-6,7,8,9-tetrahydro-2-dibenzofuranyl)-piperidine.

The 1-formyl compounds required as starting materials are prepared analogously to Example (8a) from the corresponding compounds, without the 1-substituent, described in Examples 17, 19 and 20.

EXAMPLE 24

Analogously to Example 14,
1-(2-propynyl)-4-(2,3-dimethyl-7-methoxy-5-benzofuranyl)-piperidine and its hydrochloride are obtained using 2.59 g (0.010 mol) of 4-(2,3-dimethyl-7-methoxy-5-benzofuranyl)-piperidine (c.f. Example 17),
1-(2-propynyl)-4-(2,3,7-trimethyl-5-benzofuranyl)-piperidine and its hydrochloride are obtained using 2.43 g (0.010 mol) of 4-(2,3,7-trimethyl-5-benzofuranyl)-piperidine (c.f. Example 20),
1-(2-propynyl)-4-(2,3-dimethyl-7-bromo-5-benzofuranyl)-piperidine and its hydrochloride are obtained using 3.08 g (0.010 mol) of 4-(2,3-dimethyl-7-bromo-5-benzofuranyl)-piperidine (c.f. Example 21),
1-(2-propynyl)-4-(2,3-dimethyl-7-cyano-5-benzofuranyl)-piperidine and its hydrochloride are obtained using 2.56 g (0.010 mol) of 4-(2,3-dimethyl-7-cyano-5-benzofuranyl)-piperidine (c.f. Example 22),
4-(2-propynyl)-4-(4-methoxy-6,7,8,9-tetrahydro-2-dibenzofuranyl)-piperidine and its hydrochloride are obtained using 2.85 g (0.010 mol) of 4-(4-methoxy-6,7,8,9-tetrahydro-2-dibenzofuranyl)-piperidine, and
4-(2-propynyl)-4-(4-methyl-6,7,8,9-tetrahydro-2-dibenzofuranyl)-piperidine and its hydrochloride are obtained using 2.69 g (0.010 mol) of 4-(4-methyl-6,7,8,9-tetrahydro-2-dibenzofuranyl)-piperidine.

EXAMPLE 25

Analogously to Example 14, 1-allyl-4-(2,3-dimethyl-5-benzofuranyl)-piperidine and its hydrochloride are obtained by reacting 2.29 g (0.010 mol) of 4-(2,3-dimethyl-5-benzofuranyl)-piperidine (c.f. Example 1) with 1.33 g (0.011 mol) of allyl bromide, and 1-allyl-4-(6,7,8,9-tetrahydro-2-dibenzofuranyl)-piperidine and its hydrochloride are obtained by reacting 2.55 g (0.010 mol) of 4-(6,7,8,9-tetrahydro-2-dibenzofuranyl)-piperidine (c.f. Example 8) with 1.33 g (0.011 mol) of allyl bromide.

EXAMPLE 26

Analogously to Example 14, 1-(cyclopropylmethyl)-4-(2,3-dimethyl-5-benzofuranyl)-piperidine and its hydrochloride are obtained by reacting 2.29 g (0.010 mol) of 4-(2,3-dimethyl-5-benzofuranyl)-piperidine (c.f. Example 1) with 1.49 g (0.011 mol) of cyclopropylmethyl bromide, and 1-(cyclopropylmethyl)-4-(6,7,8,9-tetrahydro-2-dibenzofuranyl)-piperidine and its hydrochloride are obtained by reacting 2.55 g (0.010 mol) of 4-(6,7,8,9-tetrahydro-2-dibenzofuranyl)-piperidine (c.f. Example 8) with 1.49 g (0.011 mol) of cyclopropylmethyl bromide.

EXAMPLE 27

2.59 g (0.01 mol) of 4-(2,3-dimethyl-7-methoxy-5-benzofuranyl)-piperidine and 2.45 g (0.05 mol) of sodium cyanide are dissolved in 13 ml of anhydrous dimethylsulfoxide and the solution is refluxed for 15 hours under nitrogen. [Method of James R. McCarthy et al, Tetrahedron Letters 1978, 5183]. Thereafter, the reaction mixture is allowed to cool to room temperature, the pH value of the reaction mixture is adjusted to 4 to 5 by adding 2 N hydrochloric acid (attention should be paid to the evolution of hydrogen cyanide) and the mixture is extracted with ethyl acetate. The extracts are dried over magnesium sulfate and the solvents are evaporated off under a waterpump vacuum. The resulting crude product is converted into the hydrochloride in methanol using hydrogen chloride. This hydrochloride is purified by recrystallising twice from methanol/ether, whereupon 4-(2,3-dimethyl-7-hydroxy-5-benzofuranyl)-piperidine hydrochloride of melting point 168°–173° is obtained.

EXAMPLE 28

2.97 g (0.01 mol) of N-methyl-3-(6,7,8,9-tetrahydro-2-dibenzofuranyl)-glutarimide are added in portions to a suspension of 7.6 g (0.020 mol) of lithium aluminium hydride in 50 ml of anhydrous ester in the course of 10 minutes at room temperature. The reaction mixture is stirred at room temperature for 3 hours and thereafter cooled to 0° and excess reducing agent is decomposed by adding 0.74 ml of water, 0.74 ml of 2 N sodium hydroxide solution and thereafter 22.4 ml of water. After 30 minutes, the mixture is filtered through diatomaceous earth, and the filtrate is dried over sodium sulfate and evaporated to dryness under a waterpump vacuum. The crude 1-methyl-4-(6,7,8,9-tetrahydro-2-dibenzofuranyl)-piperidine thereby obtained is dissolved in methanol and, by addition of an ethereal solution of hydrogen chloride, its hydrochloride is precipitated in the form of white crystals melting at 279°–281°.

The starting material is prepared as follows:

(a) 2.84 g (0.01 mol) of 3-(6,7,8,9-tetrahydro-2-dibenzofuranyl)-glutaric anhydride are added to a solution of 4.28 g (0.014 mol) of methylamine in 25 ml of toluene and 10 ml of glacial acetic acid. The mixture is refluxed for 20 hours. Thereafter, the cooled reaction mixture is poured onto 100 ml of an ice-water mixture, made alkaline by addition of 2 N sodium hydroxide solution, and extracted twice with 100 ml of ether each time. The organic phases are combined, washed with saturated sodium chloride solution, dried with sodium sulfate and evaporated to dryness under a waterpump vacuum.

N-Methyl-3-(6,7,8,9-tetrahydro-2-dibenzofuranyl)-glutarimide remains in the form of slightly brownish crystals. After recrystallisation from ether, it melts at 135° to 136°.

EXAMPLE 29

3.0 g of potassium carbonate are added to a solution of 2.9 g (0.01 mol) of 4-(6,7,8,9-tetrahydro-2-dibenzofuranyl)-piperidine in 25 ml of acetone and the mixture is stirred at room temperature for 15 minutes. 1.46 g (0.012 mol) of 3-bromo-1-propyne are added dropwise to the suspension while stirring which is thereafter continued for 15 hours at room temperature. Thereafter, the reaction mixture is filtered, the filtrate is evaporated under a waterpump vacuum, and the residue is dissolved in 100 ml of methylene chloride. The organic solution is washed 3 times with 50 ml of water each time, dried over sodium sulfate and evaporated to dryness under a waterpump vacuum. The crude 1-(2-propynyl)-4-(6,7,8,9-tetrahydro-2-dibenzofuranyl)-piperidine thereby obtained is dissolved in methanol, ethereal hydrogen chloride solution is added and the hydrochloride formed is filtered off. It has a melting point of 224°–228°.

The starting material can be prepared according to Example 9 or by the following reaction sequence:

(a) Analogously to Example (28a) using 28.4 g (0.1 mol) of 3-(6,7,8,9-tetrahydro-2-dibenzofuranyl)-glutaric anhydride and 13.9 ml of benzylamine in a mixture of 120 ml toluene and 120 ml of glacial acetic acid, N-benzyl-3-(6,7,8,9-tetrahydro-2-dibenzofuranyl)-glutatimide is obtained. After crystallisation from methylene chloride-hexane, it melts at 124°–126°.

(b) 37.4 g (0.1 mol) of N-benzyl-3-(6,7,8,9-tetrahydro-2-dibenzofuranyl)-glutarimide are reduced in a suspension of 7.6 g (0.2 mol) of lithium aluminium hydride in 500 ml anhydrous ether analogously to Example 28 to give the crude 1-benzyl-4-(6,7,8,9-tetrahydro-2-dibenzofuranyl)-piperidine, which with ethereal hydrogen chloride solution in methanol yields the hydrochloride in the form of white crystals melting at 260°–267°.

(c) 34.5 g (0.1 mol) of 1-benzyl-4-(6,7,8,9-tetrahydro-2-dibenzofuranyl)-piperidine are dissolved in 600 ml of ethanol and after adding 19.6 ml of a 18.6 percent solution of hydrogen chloride in ethanol (corresponding to 0.1 mol of hydrogen chloride) and 6.0 g of palladium-on-charcoal (5% of Pd) are hydrogenated under normal pressure and at room temperature until the uptake of hydrogen ceases. Thereafter, the catalyst is filtered off through diatomaceous earth and the filtrate is evaporated under a waterpump vacuum. Crude but crystallised 4-(6,7,8,9-tetrahydro-2-dibenzofuranyl)-piperidine is obtained which, after recrystallisation from methanol-ether, melts at 264°–267°.

What we claim is:

1. A compound of the formula I

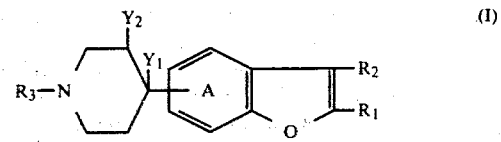

in which $R_1$ and $R_2$ independently of one another are hydrogen or lower alkyl or together are lower alkylene, $R_3$ is hydrogen, lower alkyl, lower alkenyl, lower alkynyl, cyclo-lower alkyl or cyclo-lower alkyl-lower alkyl and $Y_1$ and $Y_2$ are each hydrogen or together are an additional bond, and the ring A is not further substituted or is further substituted by lower alkyl, lower alkoxy, halogen with an atomic number of not more than 35, cyano or hydroxyl, or a pharmaceutically acceptable acid addition salt thereof.

2. A compound according to claim 1 corresponding to the formula I given in claim 1, in which $R_1$, $R_2$, $R_3$, $Y_1$ and $Y_2$ are as defined in claim 1 and the ring A is not further substituted or is further monosubstituted by lower alkyl, lower alkoxy, halogen with an atomic number of not more than 35, cyano or hydroxyl, or a pharmaceutically acceptable acid addition salt thereof.

3. A compound according to claim 1 corresponding to the general formula I given in claim 1, in which $R_1$ is methyl and $R_2$ is hydrogen or methyl, or $R_1$ and $R_2$ together are tetramethylene, $R_3$, $Y_1$ and $Y_2$ are as defined in claim 1 and the ring A is not further substituted or is further monosubstituted by lower alkyl, lower alkoxy, halogen with an atomic number of not more than 35, cyano or hydroxyl, or a pharmaceutically acceptable acid addition salt thereof.

4. A compound according to claim 1 corresponding to the general formula I given in claim 1, in which $R_1$ is methyl and $R_2$ is methyl or hydrogen, or $R_1$ and $R_2$ together are tetramethylene, $R_3$ is hydrogen or a radical according to the definition given in claim 1, which has not more than 4 carbon atoms, $Y_1$ and $Y_2$ are as defined in claim 1 and the ring A is not further substituted or is further monosubstituted by lower alkyl, lower alkoxy, halogen with an atomic number of not more than 35 or cyano, or a pharmaceutically acceptable acid addition salt thereof.

5. A compound according to claim 1 corresponding to the general formula I given in claim 1, in which $R_1$ is methyl and $R_2$ is methyl or hydrogen, or $R_1$ and $R_2$ together are tetramethylene, $R_3$ is hydrogen, lower alkyl containing not more than 4 carbon atoms, allyl, 2-propynyl, cyclopropyl or cyclopropylmethyl, $Y_1$ and $Y_2$ are as defined in claim 1 and the ring A is not further substituted or is further monosubstituted by methyl, methoxy, halogen with an atomic number of not more than 35 or cyano, or a pharmaceutically acceptable acid addition salt thereof.

6. A compound according to claim 1 corresponding to the general formula I given in claim 1, in which $R_1$ and $R_2$ are each methyl or together are tetramethylene, $R_3$ is hydrogen, methyl or 2-propynyl, and $Y_1$ and $Y_2$ are each a hydrogen atom, the ring A is not further substituted or is further monosubstituted by methyl, methoxy, halogen with an atomic number of not more than 35 or cyano, and the nitrogen-containing ring is in the 5-position or 6-position of the benzofuran ring system, or a pharmaceutically acceptable acid addition salt thereof.

7. A compound according to claim 1 which is 4-(2,3-dimethyl-5-benzofuranyl)-piperidine or a pharmaceutically acceptable acid addition salt thereof.

8. A compound according to claim 1 which is 4-(2,3-dimethyl-6-benzofuranyl)-piperidine or a pharmaceutically acceptable acid addition salt thereof.

9. A compound according to claim 1 which is 4-(6,7,8,9-tetrahydro-2-dibenzofuranyl)-piperidine or a pharmaceutically acceptable acid addition salt thereof.

10. A compound according to claim 1 which is 1-methyl-4-(2,3-dimethyl-5-benzofuranyl)-piperidine or a pharmaceutically acceptable acid addition salt thereof.

11. A compound according to claim 1 which is 1-methyl-4-(2,3-dimethyl-6-benzofuranyl)-piperidine or a pharmaceutically acceptable acid addition salt thereof.

12. A compound according to claim 1 which is 1-(2-propynyl)-4-(2,3-dimethyl-5-benzofuranyl)-piperidine or a pharmaceutically acceptable acid addition salt thereof.

13. A compound according to claim 1 which is 4-(2,3-dimethyl-7-methoxy-5-benzofuranyl)-piperidine or a pharmaceutically acceptable acid addition salt thereof.

14. A compound according to claim 1 which is 4-(2,3,7-trimethyl-5-benzofuranyl)-piperidine or a pharmaceutically acceptable acid addition salt thereof.

15. A compound according to claim 1 which is 4-(2,3-dimethyl-7-brom-5-benzofuranyl)-piperidine or a pharmaceutically acceptable acid addition salt thereof.

16. A compound according to claim 1 which is 4-(2,3-dimethyl-7-cyano-5-benzofuranyl)-piperidine or a pharmaceutically acceptable acid addition salt thereof.

17. A compound according to claim 1 which is 1-methyl-4-(6,7,8,9-tetrahydro-2-dibenzofuranyl)-piperidine or a pharmaceutically acceptable acid addition salt thereof.

18. A compound according to claim 1 which is 1-(2-propynyl)-4-(6,7,8,9-tetrahydro-2-dibenzofuranyl)-piperidine or a pharmaceutically acceptable acid addition salt thereof.

19. A pharmaceutical preparation for the treatment of emotional depression comprising a therapeutically effective amount of a compound according to claim 1 and corresponding to the formula I

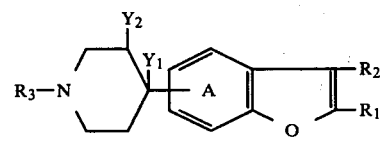

in which $R_1$ and $R_2$ independently of one another are hydrogen or lower alkyl or together are lower alkylene, $R_3$ is hydrogen, lower alkyl, lower alkenyl, lower alkynyl, cyclo-lower alkyl or cyclo-lower alkyl-lower alkyl and $Y_1$ and $Y_2$ are each hydrogen or together are an additional bond, and the ring A is not further substituted or is further substituted by lower alkyl, lower alkoxy, halogen with an atomic number of not more than 35, cyano or hydroxyl, or of a pharmaceutically acceptable acid addition salt thereof, and at least one pharmaceutical carrier.

20. A pharmaceutical preparation according to claim 19, wherein a therapeutically effective amount of a compound corresponding to the formula I given in claim 19, in which $R_1$, $R_2$, $R_3$, $Y_1$ and $Y_2$ are as defined in claim 19, and the ring A is not further substituted or is further monosubstituted by lower alkyl, lower alkoxy, halogen with an atomic number of not more than 35, cyano or hydroxyl, or of a pharmaceutically acceptable acid addition salt thereof is present.

21. A pharmaceutical preparation according to claim 19, wherein a therapeutically effective amount of a compound corresponding to the formula I given in claim 19, in which $R_1$ is methyl and $R_2$ is methyl or hydrogen, or $R_1$ and $R_2$ together are tetramethylene, $R_3$ is hydrogen, lower alkyl containing not more than 4 carbon atoms, allyl, 2-propynyl, cyclopropyl or cyclopropylmethyl, $Y_1$ and $Y_2$ are as defined in claim 19 and the ring A is not further substituted or is further monosubstituted by methyl, methoxy, halogen with an atomic number of not more than 35 or cyano, or of a pharmaceutically acceptable salt thereof is present.

22. A pharmaceutical preparation according to claim 19, wherein a therapeutically effective amount of a compound corresponding to the formula I given in claim 19, in which $R_1$ and $R_2$ are each methyl or together are tetramethylene, $R_3$ is hydrogen, methyl or 2-propynyl, and $Y_1$ and $Y_2$ are each a hydrogen atom, the ring A is not further substituted or is further monosubstituted by methyl, methoxy, halogen with an atomic number of not more than 35 or cyano, an the nitrogen-containing ring is in the 5-position or 6-position of the benzofuran ring system, or of a pharmaceutically acceptable acid addition salt thereof is present.

23. A pharmaceutical preparation according to claim 19, wherein a therapeutically effective amount of 4-(2,3-dimethyl-5-benzofuranyl)-piperidine or of a pharmaceutically acceptable acid addition salt thereof is present.

24. A pharmaceutical preparation according to claim 19, wherein a therapeutically effective amount of 4-(2,3-dimethyl-6-benzofuranyl)-piperidine or of a pharmaceutically acceptable acid addition salt thereof is present.

25. A pharmaceutical preparation according to claim 19, wherein a therapeutically effective amount of 4-(6,7,8,9-tetrahydro-2-dibenzofuranyl)-piperidine or of a pharmaceutically acceptable acid addition salt thereof is present.

26. A method for the treatment of emotional depression in a warm-blooded animal in need of such treatment comprising enteral or parenteral administration to said animal of a therapeutically effective amount of a compound according to claim 1 having the formula I defined in claim 1, or of a pharmaceutically acceptable acid addition salt thereof.

* * * * *